United States Patent [19]
Horvath et al.

[11] Patent Number: 6,002,790
[45] Date of Patent: Dec. 14, 1999

[54] METHOD FOR DETECTING AND MEASURING VOIDS IN CONDUCTOR INSULATION SYSTEMS

[75] Inventors: David A. Horvath, Ann Arbor; Steven M. Avila, Novi, both of Mich.

[73] Assignee: Advent Engineering Services, Inc., Ann Arbor, Mich.

[21] Appl. No.: 08/762,536

[22] Filed: Dec. 9, 1996

[51] Int. Cl.$^6$ ............................................. G06K 9/00
[52] U.S. Cl. ............................................. 382/141; 348/92
[58] Field of Search ................................. 382/141, 144, 382/145, 149; 348/86, 92, 125, 128; 250/339

[56] References Cited

U.S. PATENT DOCUMENTS

| | | | |
|---|---|---|---|
| 4,197,457 | 4/1980 | Cheo ..................................... | 250/339 |
| 4,555,799 | 11/1985 | Kodama et al. ...................... | 382/141 |
| 4,649,621 | 3/1987 | Dusel et al. ........................... | 382/141 |
| 4,926,452 | 5/1990 | Baker et al. ........................... | 382/150 |
| 5,293,220 | 3/1994 | Fukuda et al. ........................ | 356/394 |
| 5,761,335 | 6/1998 | Okamoto et al. ..................... | 382/141 |

OTHER PUBLICATIONS

Suthar et al, "LSCM: A Non–Destructive Diagnostic Tool for Examining the Microstructure . . . ", IEEE Insulation Magazine pp. 20–24, Jul. 1992.

"Nuclear Regulatory Commission Proposal No. SBIR–93–060", by David A. Horvath, Feb. 18, 1993, Ann Arbor, Michigan.

"Proposal To Research And Develop A Model For Predicting Electrical Insulation Life", by David A. Horvath, Apr. 14, 1995, Ann Arbor, Michigan.

"Partial Discharge—Part XI: Limitations To PD As A Diagnostic For Deterioration And Remaining Life", by C. Laurent and C. Mayoux, IEEE Electrical Insulation Magazine, Mar./Apr. 1992, vol. 8, No. 2.

"Partial Discharge XVII: The Early History Of Partial Discharge Research", by David A. Nattrass, IEEE Electrical Insulation Magazine, Jul./Aug. 1993, vol. 9, No. 4.

"Influence Of Space Charge Buildup On The Transition To Electrical Treeing In PE Under AC Voltage", by M. Mammeri, C. Laurent, J. Salon, IEEE Electrical Insulation Magazine, Feb. 1995, vol. 2, No. 1.

*Primary Examiner*—Christopher S. Kelley
*Attorney, Agent, or Firm*—Gregory L. Bradley

[57] ABSTRACT

A method of detecting and measuring voids in insulation material includes: providing a sample of insulation material; providing an imaging system for generating an image of the sample of the insulation material; analyzing the image to detect the presence of voids therein; and measuring the voids present in the sample to determine their size and density. Preferably, a nondestructive imaging system is utilized to detect and measure the voids.

11 Claims, 21 Drawing Sheets

| Sample Number | Sample Description | Void Size (Average) | Void Density[1] (voids/cm$^3$) | Testing Method |
|---|---|---|---|---|
| 1 to 5 | Various | Indeterminate | Indeterminate | Ultrasound |
| 3 | Aged PE | Indeterminate | Indeterminate | Ultrasound |
| 5 | Aged EPR | Indeterminate | Indeterminate | C SAM |
| 3 | Aged PE | <75 μm | 140 | C SAM |
| 3 | Aged PE | 175 μm | 30 | C SAM |
| 8 | New EPR | Indeterminate | Indeterminate | C SAM |
| 1 | Aged PE | 7.5 μm | 500 | Optical Microscopy |
| 3 | Aged PE | 3 μm | 1000 | Optical Microscopy |
| 8 | New EPR | 10 μm | 100 | Optical Microscopy |
| 1 | Aged PE | 6 μm | 500 | Optical Microscopy |
| 3 | Aged PE | 12.5 μm | 225 | Optical Microscopy |
| 3 | Aged PE | 5 μm | 250 | Optical Microscopy |
| 1 | Aged PE | 6.25 μm | 660 | SEM |
| 1 | Aged PE | 3.25 μm | 300 | SEM |
| 6 | New PE | 0.4 μm | 3000 | SEM |
| 8 | New EPR | 4.5 μm | 700 | SEM |
| 8 | New EPR | 2.25 μm | 1000 | SEM |

| Sample No. | Insulation Type | Insulation Thickness | Manufacturer | Size | Voltage Rating | Comment(s) |
|---|---|---|---|---|---|---|
| 1 | XLPE (Polyethylene) | 280 Mils | Essex | 750 MCM | 28 kV | Cable was used, dated 1972 |
| 2 | XLP (Polyethylene) | 280 Mils | Pirelli | 750 KCMIL | 28 kV | Cable was used, dated 1981 |
| 3 | XLPE (Polyethylene) | 185 Mils | Essex | 1/0 AWG | 15 kV | Cable was used, Grounded Neutral, dated 1976 |
| 4 | XHHW-2 (Polyethylene) | 75 Mils | Service Wire Company | 350 MCM | 600 Volt | Cable does not appear used, date unknown |
| 5 | EPR (Ethylene Propylene Rubber) | 75 Mils | Okonite | 2/0 AWG | 600 Volt | Cable appears used, provided single phase conductor only, date unknown |
| 6 | XHHW-2 (Polyethylene) | 50 Mils | Rockbestos | 3/C-1/0 AWG | 600 Volt | Cable is new, 3/C jacketed sample provided, dated 1995 |
| 7 | SR-2 (Silicone Rubber) | 90 Mils | Rockbestos | 4/0 AWG | 600 Volt | Cable is new, rockhide braid cable, dated 1995 |
| 8 | EPR Ethylene Propylene Rubber) | 60 Mils | Rockbestos | 1/0 AWG | 600 Volt | Cable is new, dated 1995 |

Figure 2

| Sample Number | Sample Description | Void Size (Average) | Void Density[1] (voids/cm³) | Testing Method |
|---|---|---|---|---|
| 1 to 5 | Various | Indeterminate | Indeterminate | Ultrasound |
| 3 | Aged PE | Indeterminate | Indeterminate | Ultrasound |
| 5 | Aged EPR | Indeterminate | Indeterminate | C SAM |
| 3 | Aged PE | <75 μm | 140 | C SAM |
| 3 | Aged PE | 175 μm | 30 | C SAM |
| 8 | New EPR | Indeterminate | Indeterminate | C SAM |
| 1 | Aged PE | 7.5 μm | 500 | Optical Microscopy |
| 3 | Aged PE | 3 μm | 1000 | Optical Microscopy |
| 8 | New EPR | 10 μm | 100 | Optical Microscopy |
| 1 | Aged PE | 6 μm | 500 | Optical Microscopy |
| 3 | Aged PE | 12.5 μm | 225 | Optical Microscopy |
| 3 | Aged PE | 5 μm | 250 | Optical Microscopy |
| 1 | Aged PE | 6.25 μm | 660 | SEM |
| 1 | Aged PE | 3.25 μm | 300 | SEM |
| 6 | New PE | 0.4 μm | 3000 | SEM |
| 8 | New EPR | 4.5 μm | 700 | SEM |
| 8 | New EPR | 2.25 μm | 1000 | SEM |

Figure 21

METHOD FOR DETECTING AND MEASURING VOIDS IN CONDUCTOR INSULATION SYSTEMS

BACKGROUND OF THE INVENTION

The present invention relates generally to the field of conductor insulation and, more particularly, to a method for detecting and measuring voids in conductor insulation systems of a size considerably smaller than would generally be considered an obvious manufacturing defect.

Voids and gaseous cavities originate in conductor insulation systems through a variety of mechanisms, including normal as well as improper manufacturing processes, severe or cumulative mechanical and environmental stresses, and differential thermal expansions.

As explained in more detail below, when a conductor insulation system contains voids or cavities of a sufficient size and density, electrical discharges occur therein. These discharges result in an increase in current flow through the insulation between the conductor and ground or between two adjacent conductors, and a consequent reduction in the amount of current which is able to be transmitted through the conductor(s).

Further, the presence of voids or cavities of a sufficiently large size within a conductor insulation system (when subjected to an electric field or potential of sufficient magnitude) facilitates the initiation and growth of "electrical trees," which also detrimentally affect the insulation system's conductivity and projected life.

An electrical tree consists of a number of tiny hollow channels that extend and propagate from voids or impurities present in a conductor insulation system. The hollow channels can contain or allow considerable unstable discharges which, in time, may initiate further tree growth until cable failure occurs.

As explained above, when voids are present in a conductor insulation system, the insulating walls in effect "erode" in time and cause dielectric breakdown.

Three processes cause this dielectric breakdown: (1) bombardment of the void's walls by ions and electrons produced when gases within the void become ionized (i.e., corona breakdown); (2) heat generated by the corona breakdown process; and (3) chemical reactions within the void, due to the formation of ozone.

Conventionally, manufacturers have been responsible for testing conductor insulation systems, such as cables, for obvious voids (i.e., manufacturing defects of a magnitude sufficient to allow immediate or premature cable insulation failure) before shipping the cables from the factory. The manufacturers' favored production test (i.e., the partial discharge test) is performed to cable specifications prepared by the Association of Edison Illuminating Companies (AEIC). The AEIC has only promulgated specifications for medium and high-voltage cable; currently, there are no specifications for low-voltage (i.e., 600 to 2000 Volts) cable, which is the most commonly used cable today.

The partial discharge test measures the discharge magnitude (Q), which is measured in pico-coulombs. Manufacturers are required to maintain the discharge magnitude below a specific level (i.e., not greater than 5 pico-coulombs) before shipping the cable.

The industry has accepted the partial discharge test because it uses the simplest measurement that can be made to date, and it can detect insulation degradation. However, because of the many cable failures that occur due to voids being present in cable, often after installation and over time, it is evident that the partial discharge test and other existing testing methods are not able to locate voids that can cause subsequent failure.

As can be appreciated, the goal of current testing methods, including the partial discharge test, is to ascertain whether partial discharges are present in a conductor insulation system before it is shipped to customers. Also, there are currently no nondestructive tests available to detect voids or other defects, or to estimate system condition, in installed conductor insulation systems. Consequently, the conventional approach to evaluating cable condition is by a "post-mortem" analysis after the cable has failed.

Because the presence of voids can ultimately lead to conductor insulation system failure, those industries, such as the nuclear power industry, where the integrity of power and control systems implemented by conductor insulation systems is critical, have long desired a method for assessing insulation integrity degradation (which is related to void size and density), and for identifying potential problems related thereto, in new and installed conductor insulation systems before partial discharge occurs.

SUMMARY OF THE INVENTION

The present invention provides one or more methods for detecting and measuring voids in conductor insulation systems. By inspecting and monitoring conductor insulation systems for voids before there is any suspicion or occurrence of system degradation, the presence of potentially harmful voids may be detected before discharge and insulation malfunction or failure occurs.

According to a first aspect of the present invention, a method of detecting and measuring voids in conductor insulation material includes: providing a sample of an insulation material; providing an imaging system for generating an image of the sample of the insulation material; analyzing the image to detect the presence of voids therein; and measuring the voids present in the sample to determine their size and density.

According to a second aspect of the present invention, a method of establishing void parameters for insulation material includes: providing a plurality of samples of an insulation material; providing an imaging system for generating at least one image of each of the plurality of samples; analyzing the image of each of the plurality of samples to detect the presence of voids therein; analyzing the voids to determine one or more void parameters for each of the plurality of samples; and comparing the one or more void parameters for each of the plurality of samples to determine the limiting void parameters among the samples (where the limiting parameters may be considered the combination of largest void size and highest void density).

According to a third aspect of the present invention, a method of detecting and measuring voids in insulation material includes: providing at least one sample of an insulation material; providing a nondestructive imaging system for generating one or more images of the at least one sample of the insulation material; analyzing the one or more images to detect the presence of voids therein; measuring one or more of at least the size and density of the voids present in the at least one sample; comparing the sample void parameters of at least size and density and determining the limiting parameters among the measured samples thereof; and deriving a model for the level of operability of the insulation material as a function of one or more of at least the size and density of the voids detected in the at least one sample and the insulation system's design or required electric field potential.

By periodically inspecting and monitoring installed conductor insulation systems for the presence of potentially harmful voids, which can lead to the initiation and growth of electrical trees, insulation degradation can be detected, and the system replaced or repaired, before the insulation system malfunctions or fails.

These and other features and attendant advantages of the present invention will be further understood upon consideration of the following detailed description of various embodiments of the present invention, taken in conjunction with the accompanying drawings.

BRIEF DESCRIPTION OF THE DRAWINGS

FIG. 2 is a table describing various characteristics of the cable samples tested according to the present invention.

FIG. 21 is a table showing test results for polyethylene (PE) and ethylene propylene rubber (EPR).

DETAILED DESCRIPTION OF THE PRESENTLY PREFERRED EMBODIMENTS

As discussed in greater detail below, the present invention provides one or more destructive and nondestructive methods for detecting and measuring micron-sized voids inside conductor insulation materials.

Preferably, the nondestructive methods utilize conventional ultrasound testing and acoustical microscopy and the destructive methods utilize optical and scanning electron microscopy.

Figure 1:
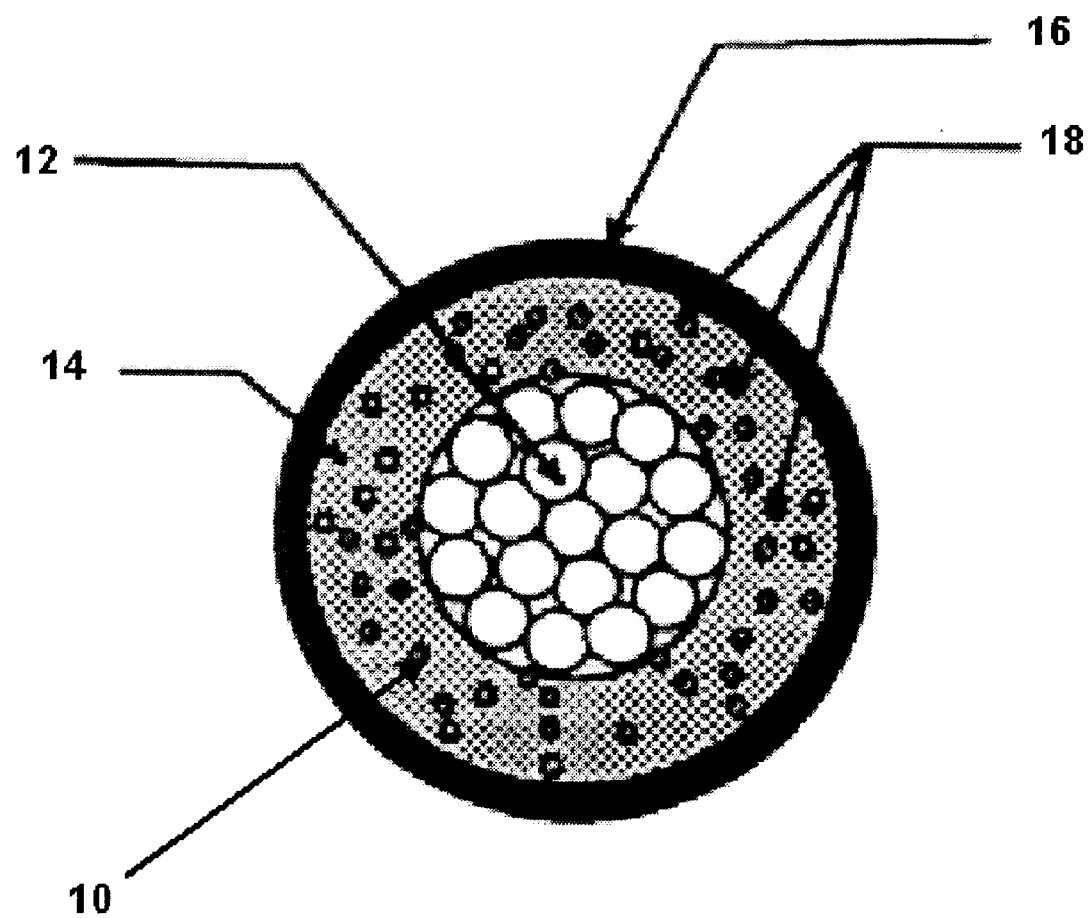
FIG. 1 is a lateral cross-sectional view of a conventional conductor insulation system showing voids present in the insulation material thereof.

Turning now to the drawings, FIG. 1 illustrates a conductor insulation system 10 having one or more conductors 12 surrounded by a suitable conductor insulation material 14. To protect the conductor insulation material 14 from the environment, a cable jacket 16 of suitably durable and insulative material is disposed therearound.

As shown in FIG. 1, the conductor insulation material 14 includes a number of voids 18 therein. As discussed above, electrical discharges may occur in the voids 18, which may ultimately result in cable malfunction or failure. Further, the voids 18 may cause electrical trees to appear and grow in the insulation material 14, which can also lead to the rapid breakdown of the conductor insulation system 10.

As shown in FIG. 2, eight (8) cable samples were tested to detect and measure cable insulation voids as small as 2.5 $\mu$n (0.0001 inch) in diameter, with a density equal to or less than 2 voids per $cm^3$ (approximately 30 voids per cubic inch).

Samples 1 through 5 consisted of old cables recovered from a power plant. As shown in FIG. 2, these samples had the following characteristics: (1) polyethylene (XLPE) and ethylene propylene (EPR) insulation; (2) different manufacturers; (3) medium and low-voltage ratings; (4) effects related to pre-operational use; and (5) effects related to natural aging of up to 23 years.

Samples 5 through 8 consisted of new cables provided by Rockbestos Cable Manufacturing Company. These samples included low voltage-rated cables having polyethylene (XLPE), ethylene propylene (EPR) and silicone rubber insulation.

The objectives of the tests were two-fold: (1) to verify that voids exist within all conductor insulation material; and (2) to ascertain void size and the level of void uniformity.

Each of the testing methods, including the experimental results derived from the use thereof, is described below.

Ultrasound Testing

Ultrasound waves consist of vibrational waves that are transmitted at a frequency higher than the hearing range of the normal human ear, which is typically 20,000 cycles per second (cps) or 20 KHz.

Ultrasound waves travel with ease in uniform solids and low viscosity liquids, but are quickly attenuated by voids or gas pockets. The ultrasound frequency for small flaw or void detection may be set in the range of 1 to 10 MHz.

Essentially, ultrasound testing relies on the attenuation of sound waves. However, excessive ultrasound attenuation in some materials can severely limit the use of ultrasound as a detection method when searching for small flaws or voids. The major causes of ultrasound attenuation include scattering, absorption (i.e., thermoplastic damping), and diffraction.

An electromechanical transducer, such as a piezoelectric crystal, may be used to generate ultrasound waves for flaw detection.

Significantly, ultrasound waves have the following characteristics: (1) they travel long distances in solid materials; (2) they travel in well-defined sonic beams; (3) their velocity is constant in homogeneous materials; (4) the energy from the first wave train is dissipated before the next train is introduced; (5) they are reflected at interfaces where elastic and physical properties change and are also refracted when elastic properties change; and (6) they may change their mode of vibration or be subject to mode conversion at material interfaces.

The relationship between frequency, wavelength, and wave velocity of the material is given by the following equation:

$$C = \lambda \times f \quad [\text{Eq. 1}]$$

where:

C=velocity (cm/s)

λ=wavelength (cm)

f=frequency (cps)

From equation (1), it can be appreciated that velocity varies directly with wavelength and frequency, but wavelength and frequency vary inversely with each other. Velocity is the speed at which ultrasonic vibrations pass through a material, and it is dependent on the elastic properties of the material and the mode of vibration. Thus, the elasticity and density of a material determines its sound velocity.

Ultrasound testing is widely used by industry for quality control and equipment integrity studies. Uses for ultrasound testing include flaw detection and wall thickness testing of pipes and pressure vessels.

Conventional ultrasound techniques are normally used to detect voids in metallic and composite materials. The ultrasonic energy travels into the test material from the outer surface thereof via a coupling medium. By determining the amount of ultrasonic energy that is transmitted through the test material, the condition of the test material (i.e., the quantity of voids therein) may be assessed.

Conventional ultrasound testing techniques may be limited by a number of factors, including the attenuation characteristics of certain materials, and the difficulty in gaining access to the insulation systems to be tested. Modern imaging methods, such as acoustical holography, have not overcome these limitations. However, by using information conveyed by the phase and amplitude of ultrasonic waves, the imaging method can allow cross-sectional and three-dimensional imaging of voids in three-dimensional objects.

Flaws in pipes and vessels are detected using an ultrasonic transducer, which generates sound wave trains. If flaws are present in the metal, acoustic mismatch occurs and some of the ultrasonic energy is reflected back to the transducer. These reflected sound waves are converted to electrical pulses within the transducer. The distance of the void or flaw from the surface can then be estimated using the relationship of the pulse amplitude.

Various cable samples were tested for voids using convention ultrasound techniques. The following discussion summarizes the experimental procedures and results of the conventional ultrasound examinations.

Test 1

The samples were tested by means of a pulse echo testing system, which is similar to conventional ultrasound testing. The cable samples were placed in a "V" notched fixture and immersed in water. The transducer was then aligned radially to the cable. The instrument gain was adjusted. The steps were repeated for different transducers and cable types.

Figures 3A, 3B:
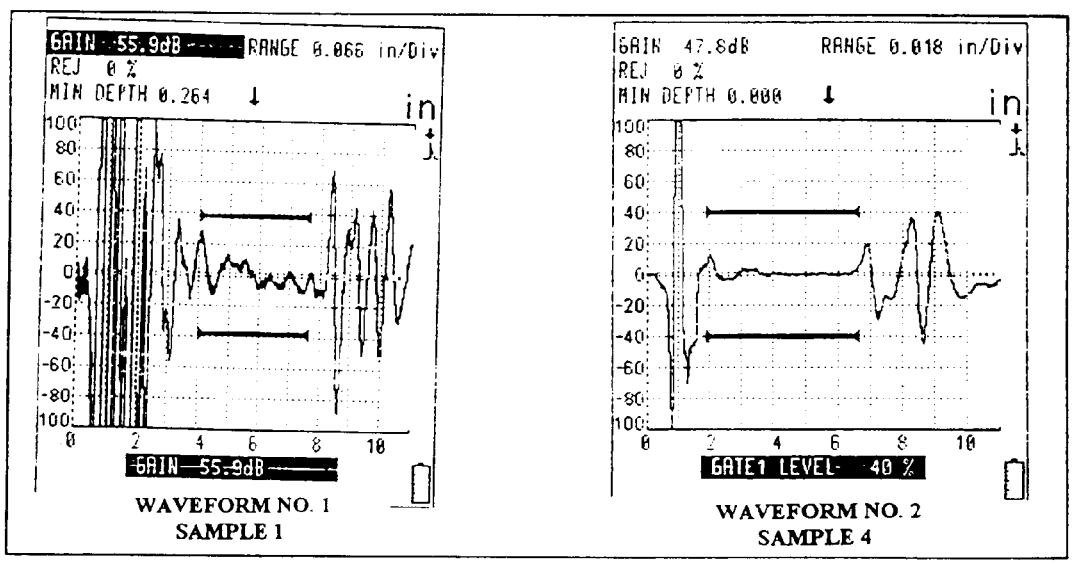
FIG. 3 is a graphic representation of the results of Ultrasound Test 1.

As shown in FIG. 3, the y-direction corresponds to the acoustic amplitude and the x-direction corresponds to the time (μ sec). Samples 1, 2, and 3 fall into a category represented by FIG. 3, Waveform #1, which is an oscilloscope display made with a 2.25 MHz transducer.

The first large interface echo on the left, identified as Reflection No. 1 (between approximately 0.2 and 2.25 μs), is the sound reflection from the secondary echo received at surface entry (outside diameter) of the cable jacket. The next large signal, identified as Reflection No. 2 (between approximately 8 and 10 μs), is the sound reflection from the secondary echo received at the metal interface between the conductor and conductor insulation.

The thick parallel (horizontal) black lines between approximately 4 and 8 μs illustrate the gated interval. The gated interval represents the thickness of the conductor insulation. Reflections within this interval represent material discontinuities or voids inside the insulation material. The amplitude of the reflection characterizes the size of the void. The estimated void size using this waveform is somewhere between 0.020" and 0.040".

FIG. 3, Waveform #2, represents an oscilloscope display obtained with a 10 MHz transducer for Samples 4 and 5. Similar to the previous explanation, the first large interface echo on the left, identified as Reflection No. 1 (between approximately 0.75 and 2 μs), is the sound reflection from the secondary echo received at surface entry (outside diameter) of the cable jacket. The next large signal, identified as Reflection No. 2 (between approximately 7 and 9 μs), is the sound reflection from the secondary echo received at the metal interface, between the conductor and conductor insulation.

The thick parallel (horizontal) black lines between approximately 2 and 6.75 μs illustrate the gated interval. This interval represents the thickness of the conductor insulation, whereby any reflections within this interval represent material discontinuities or voids. As before, the amplitude of the reflection characterizes the size of the void. As can be seen, the amplitude of reflections are very small, making it difficult to assess the plot for a minimum detectable void size. At best, this plot shows that sound waves at 10 MHz have the required energy to penetrate through the outside cable jacket material and propagate through the conductor insulation material.

Samples 6 through 8 were not tested with the above technique for various reasons, which are explained below. Sample 6 was not inspected with this technique because of its irregular, asymmetrical interior. Sample 7 was not inspected because of the fabric coating surrounding he insulation material. Sample 8 had a two-layer jacket, with the layers not appearing to be consistently bonded to one another. Because the inconsistent bonding would most likely distort the results of the testing on the insulation material thereunder, Sample 8 was not tested.

Test 2

The samples were tested by a newly-developed, real-time software application called the FlexSCAN System, which was developed by Sonix, Inc. The FlexSCAN System was derived from the older C-scan ultrasound system and developed into an imaging system software.

The cable samples were immersed in a water bath. The transducer was then moved over the particular sample to maximize reflection from its outside diameter. The transducer was then disposed at the optimum working distance from the sample. The instrument gain was adjusted as required to raise inside diameter reflection to 80% screen (i.e., to optimize the viewing axes on the monitor). The "time of flight" of the reflection was then measured. The above steps were repeated for different frequency transducers on jacket and insulation areas.

Figure 4:
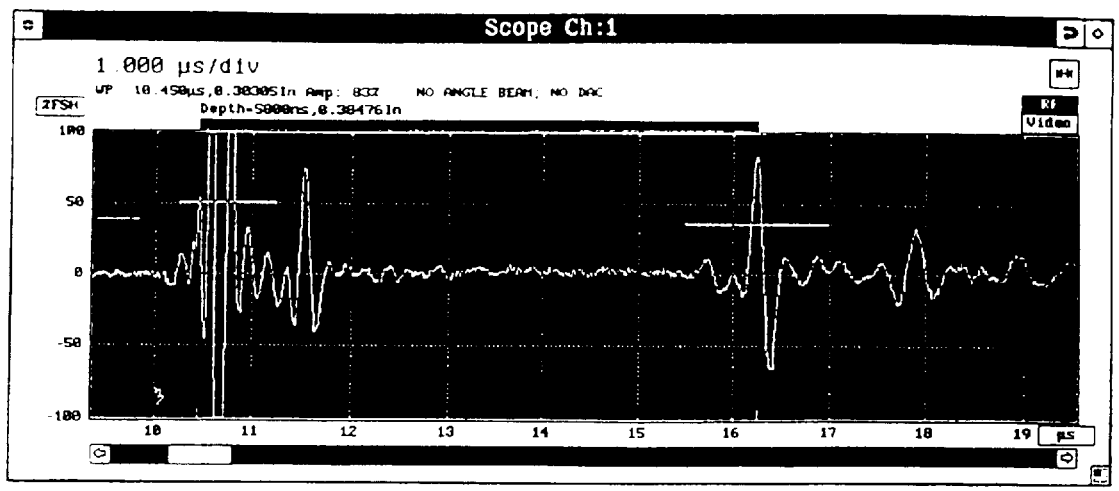
FIG. 4 is a graphic representation of the results of Ultrasound Test 2.

As shown in FIG. 4, the y-direction corresponds to the acoustic amplitude and the x-direction corresponds to the time (μ sec). The black and white plot of FIG. 4 shows an oscilloscope display of the ultrasonic signal of Sample 3 using a 10 MHz transducer.

The first large signal on the left, identified as Reflection No. 1 (at ≈10.75 μs), is the sound reflection from the entry surface (outside diameter) of the cable jacket. The next signal, identified as Reflection No. 2 (at ≈11.5 μs), is the reflection from the jacket to the insulation interface. The last signal, identified as Reflection No. 3 (at ≈16.25 μs), is the reflection from the insulation to the conductor interface.

The signal reflection between approximately 11.75 and 16 μs is the section that displays the wave propagation through the conductor insulation material. Therefore, this section will show signal reflections from material discontinuities such as voids where there is a mismatch of acoustic properties.

As can be seen in FIG. 4, it was difficult to assess the plot for voids within the insulation material. At best, this plot shows that sound waves at 10 MHz have the required energy to penetrate through the outside cable jacket material and propagate through the conductor insulation material.

Acoustical Microscopy

The essential component in acoustical microscopy is the transducer. As with conventional ultrasound testing, acoustical microscopy requires a coupling medium—usually water—to transfer the focused acoustic wave from the transducer to the specimen being examined.

Acoustical microscopy is a general term applied to high-resolution, high-frequency ultrasonic testing techniques that produce images of features beneath the surface of a test specimen. Because ultrasonic energy requires continuity to propagate, discontinuities such as voids can interfere with transmission or reflection of ultrasound signals. This makes it possible to reveal voids within a material medium.

Because an acoustic microscope operates at very high frequencies, it is possible to achieve resolution comparable to that of a conventional optical microscope. The acoustic microscope has also been found to be compatible with most polymers. This is important, because compatibility of a material is limited by ultrasound attenuation caused by scattering, absorption, or internal reflection.

As stated earlier, conventional ultrasound techniques operate up to 10 MHz. Acoustic microscopes operate up to and beyond 1 GHz, where the wavelength is very short and the resolution correspondingly high. Because the frequency of an acoustic wave is proportional to the resolution of a defect but inversely proportional to the depth of penetration, acoustical microscopy has a distinct advantage over conventional ultrasound testing. For example, a low-frequency ultrasound transducer will permit deep penetration of the acoustic wave at the expense of the resolution; a high-frequency acoustical transducer, conversely, will resolve smaller defects at lesser depths in the material.

At first, it was believed that the highest frequencies would dominate acoustic microscopy applications. However, because of the high attenuation of materials, the frequency range from 10 to 100 MHz is most extensively used.

There are presently three types of acoustic microscopes: Scanning Acoustic Microscope (SAM), C-mode Scanning Acoustic Microscope (C-SAM), and Scanning Laser Acoustic Microscope (SLAM). Each of these apparatuses has a specific range of applications.

SAM is primarily a reflection microscope that generates very high-resolution images of the surface and near-surface of the test object. The frequency operating range is between 100 MHz to 2 GHz. Penetration depth is limited.

SLAM creates real-time images of a test object throughout its entire thickness. The depth of penetration is limited by the acoustic attenuation characteristics of the material. The frequency operating range is between 10 to 500 MHz.

C-SAM is primarily a pulse echo (reflection) microscope. The transducer alternately acts as a transmitter and a receiver that generates images by mechanically scanning the transducer in a raster pattern over the test object. C-SAM is an ideal method for investigating internal images at specific depths, and was chosen for the acoustical microscopy examination. The frequency operating range is between 10 to 100 MHz.

Figure 5:
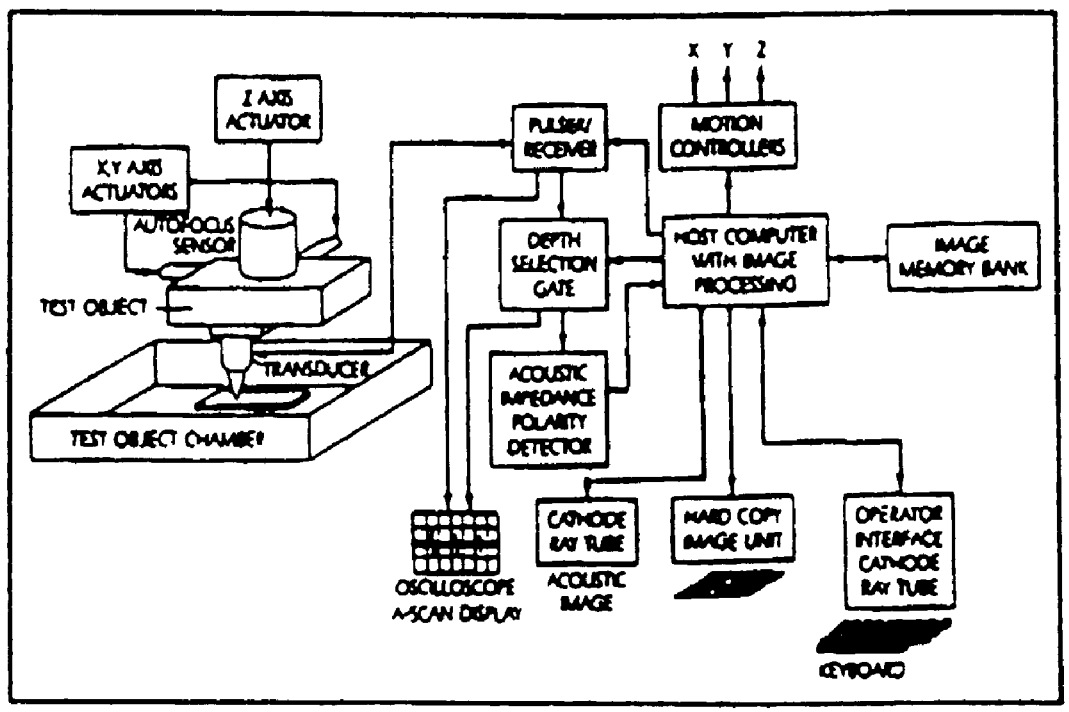
FIG. 5 is a schematic representation of a C-SAM operating system and its attendant components.

C-SAM analysis uses a single-focused acoustic lens to mechanically raster scan a tiny "dot" of ultrasound over the sample. As ultrasound is introduced (pulsed) into the sample, a reflection (echo) is generated at each subsequent interface and returned to the transmitting transducer for processing. High-speed digital signal processing allows information to be gathered from multiple levels within the sample being examined. Internal images can be generated for specific depths, cross-sections, or for the entire thickness of the test sample. A diagram of the C-SAM operating system and components are shown in FIG. 5.

By using the C-SAM apparatus with an integral digital analyzer, voids as small as 100 microns in size could be detected and measured. Because the C-SAM technique requires that cross-hairs be placed on the outside edges of a void, the size of void that can be measured is necessarily limited by the size of the crosshairs.

A C-SAM Series D6000 acoustic microscope was used to examine insulation Samples 3, 5 and 8 for voids.

Test Sample 5

Sample 5 (unaltered) was examined to determine the level of void resolution resulting from penetration through an entire cable assembly. The following describes the procedure for this examination.

Cable Sample 5 was secured to a testing plate and immersed in a bath of water. A 15 MHz transducer was attached to the microscope. The front end gain was set. Sound level was focused at the top of the sample by mechanically moving the transducer up and down to maximize the sound wave amplitude generated by the transducer. The scan was then performed. An electronic gate was established by viewing the oscilloscope A-scan display (waveform plot) and selecting a gate between the reflection waveform at the jacket interface and the reflection waveform at the conductor interface. (The selected gate interval determines the area to be examined.) An acoustic image of the sample was observed on the CRT. The front-end gain was adjusted and the scan repeated until the magnification was optimized for imaging voids.

Figure 6:
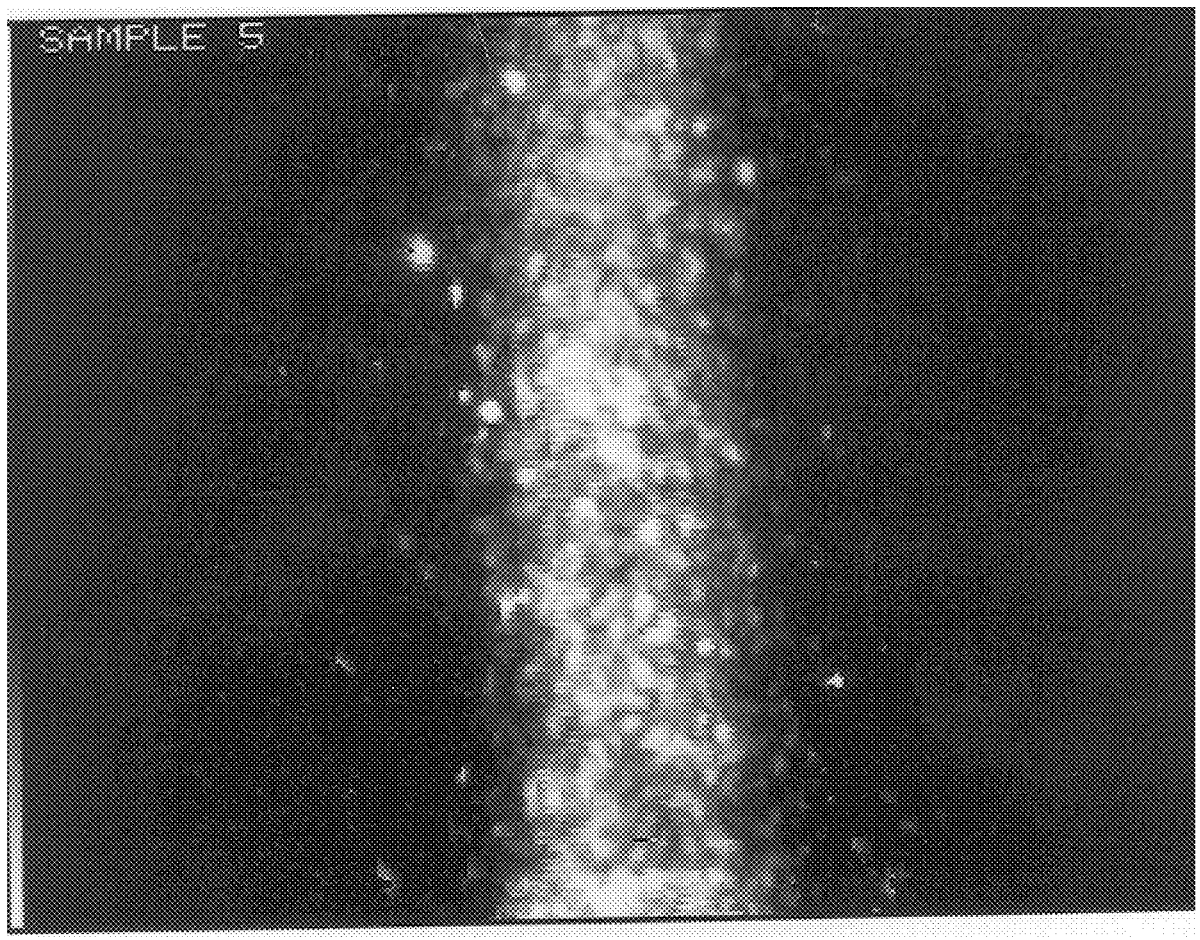
FIG. 6 is an acoustic image of Sample 5 at 15 MHz.

FIG. 6 shows the acoustic image of Sample 5 (ethylene propylene rubber) at 15 MHz, where the entire cable sample was immersed in a bath of water. The bright spots in this figure illustrate internal images of voids from sound waves at 15 MHz, penetrating the cable jacket and reflecting from the outer boundaries.

Test Samples 3 and 8

Thin wafers of Samples 3 and 8, cut with a razor blade, were provided for examination. These specimens measured approximately ¼-inch wide by ½-inch long by ⅛-inch thick. The following procedure was used for this examination.

The wafers of Samples 3 and 8 were secured approximately one-inch apart on a testing plate with tape and immersed in a bath of water. A 50 MHz transducer was attached to the microscope. The front-end gain was set. Sound level was focused at the top of one of the samples by mechanically moving the transducer up and down to maximize the sound wave amplitude generated by the transducer. The scan was performed. An electronic gate was established by viewing the oscilloscope A-scan display (waveform plot) and selecting a gate between the reflection waveform at the top-surface interface and the reflection waveform at the bottom-surface interface. (The selected gate interval determines the area to be examined.) An acoustic image of the sample was observed on the CRT. The above steps were repeated for Samples 3 and 8.

Figure 7:
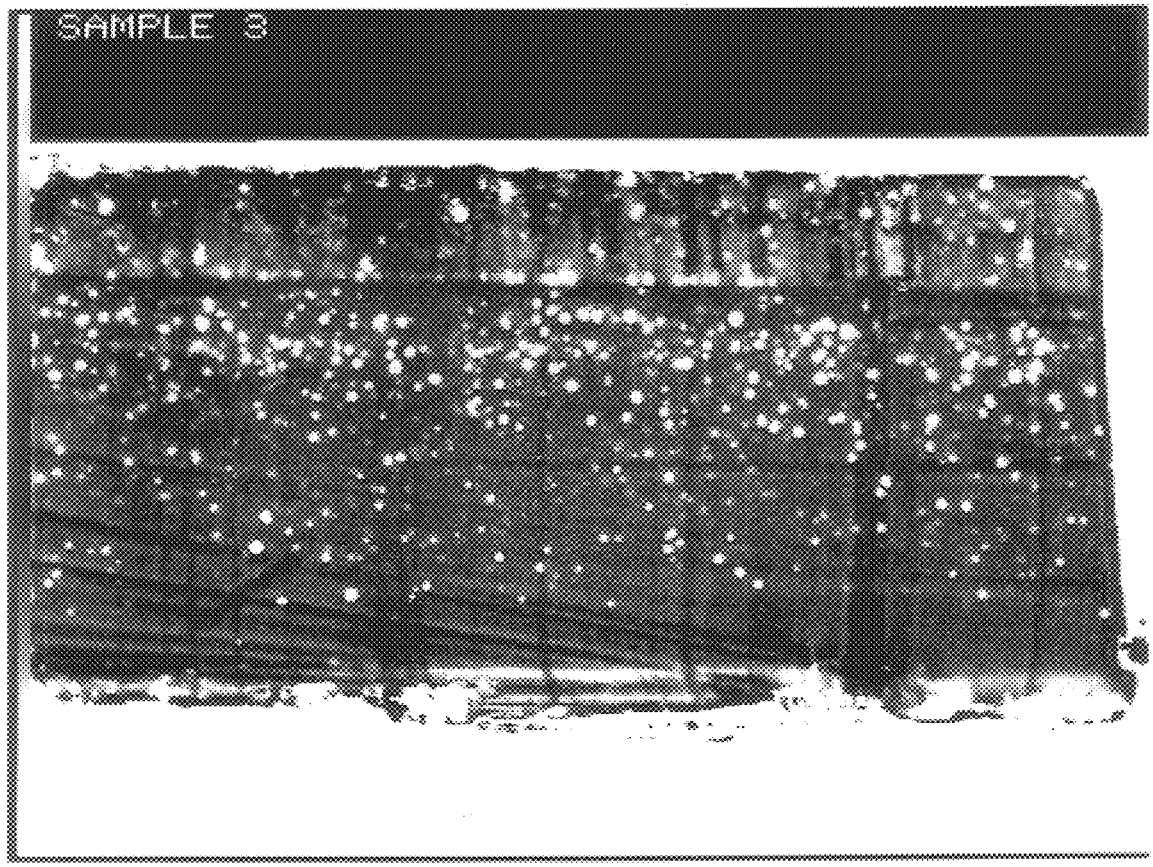
FIG. 7 is an acoustic image of Sample 3.
Figure 8:
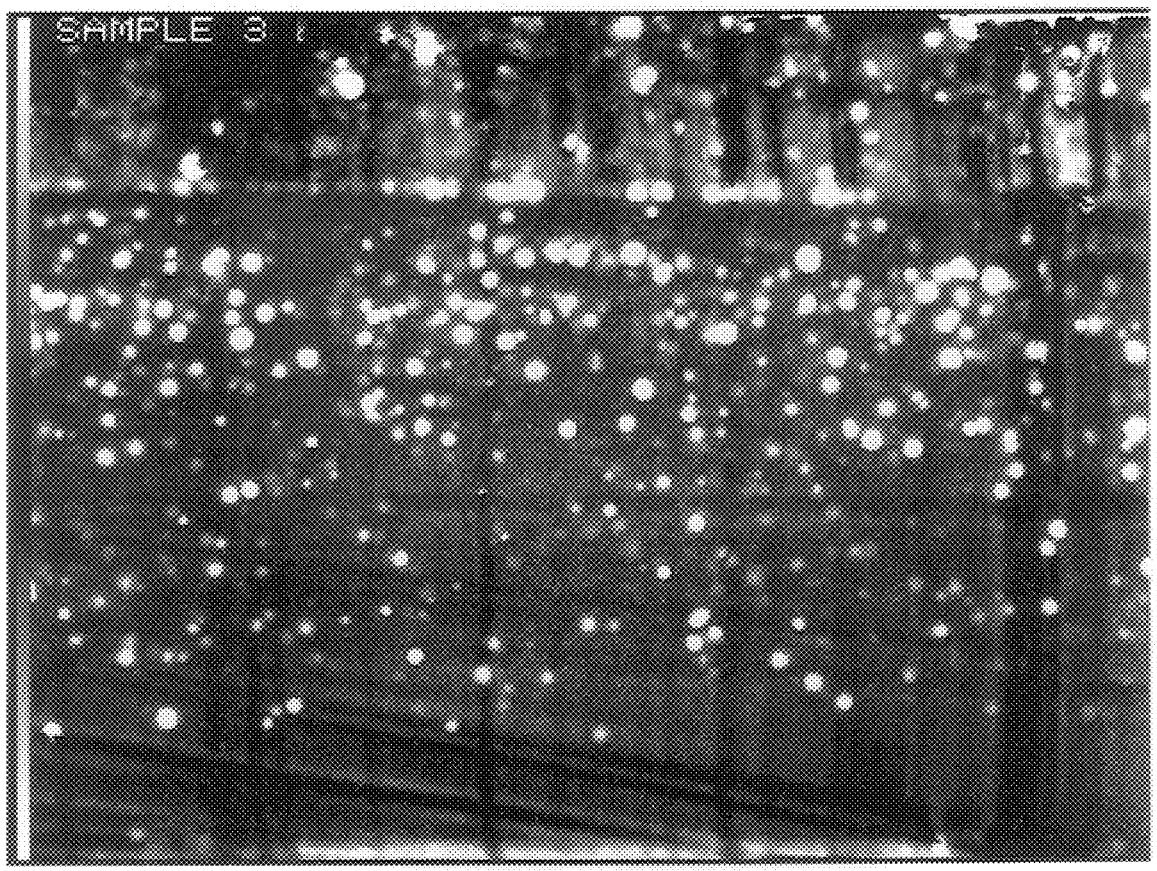
FIG. 8 is a magnified version of FIG. 7.

The bright spherical spots shown in FIGS. 7 and 8 (FIG. 8 is a magnified version of FIG. 7) correspond to the reflection of sound waves from voids in Sample 3. Because penetration of the cable jacket was not a concern for Sample 3, a higher frequency transducer could be used. The high-frequency transducer provided a higher resolving power and a more distinct image.

Figure 9:
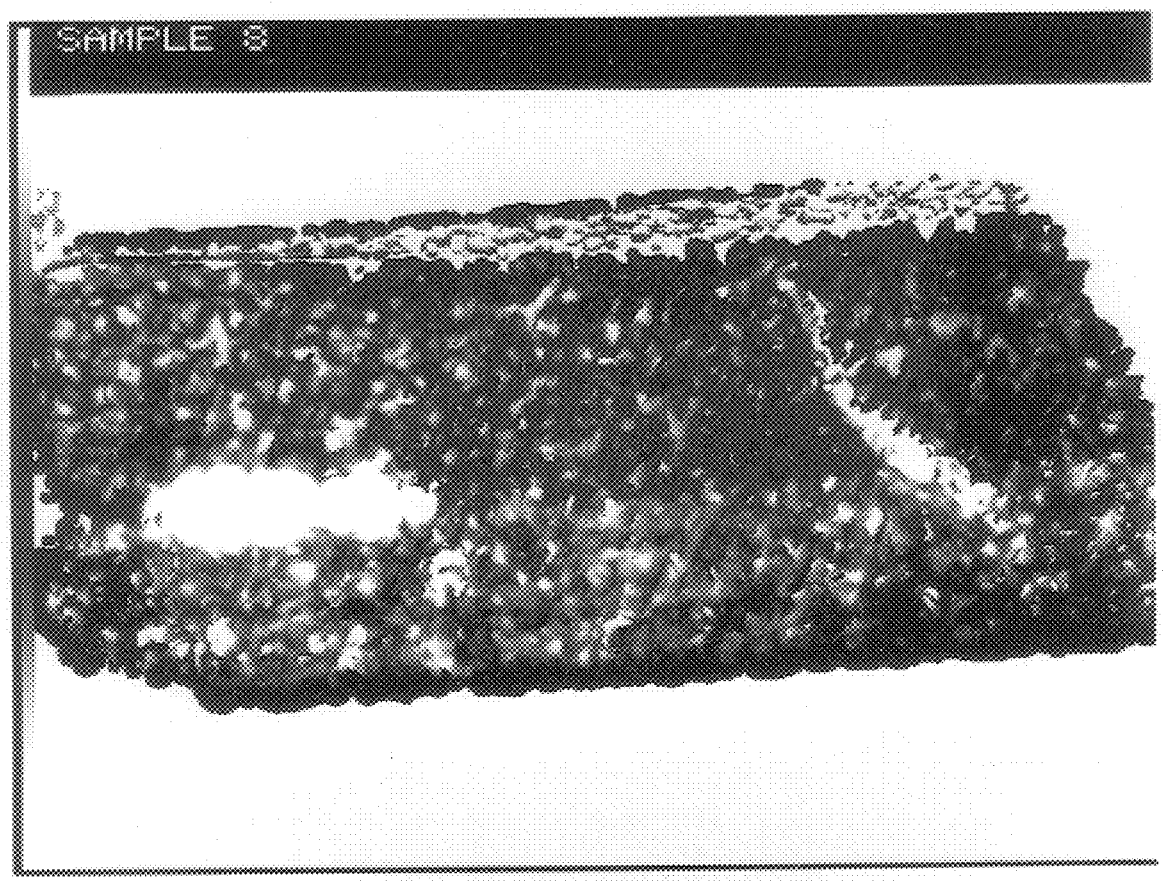
FIG. 9 is an acoustic image of Sample 8 at 50 MHz.
Figure 10:
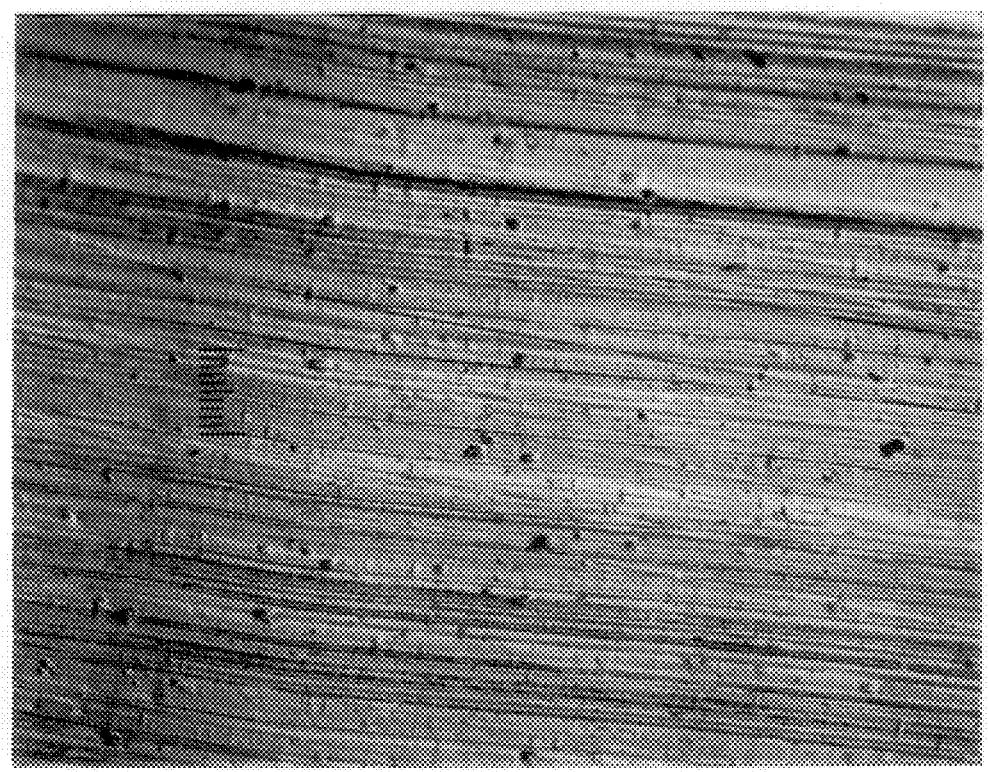
FIG. 10 is an optical image of Sample 1 at 200×.

An acoustic image from the cross-section specimen of Sample 8, taken with a 50 MHz transducer, is shown in FIG. 9. The white speckles in FIG. 9 represent voids in the insulation material.

The bright spherical-shaped spots of FIGS. 6, 7 and 8 are classified as voids because they correspond to high amplitude reflections from the interface of a high-acoustic impedance material from inside the void or impurity pocket, such as a gaseous cavity, air bubble, or other void type. Differences in acoustic impedance between air or gas and a solid material cause most of the ultrasonic energy to be reflected at the surface boundary of a gaseous cavity, air bubble, or void.

The bright spots are reflections of higher signal levels from the interface of voids. These spots have a lighter feature because the sound waves are reflected back to the transducer at a faster rate. This is due to the different optical properties between the void and solid insulating material. The bright acoustical images are therefore reflected energy signals formed in the pattern of the void.

The dark features around the void images represent waves passing through the insulation material. As the waves travel through the insulation, part of the energy is absorbed because of the attenuation behavior or the progressive decrease in vibrational energy through the material. The remaining vibrational energy received by the transducer is then several times smaller in magnitude than the energy level transmitted by the transducer.

An important material parameter affecting the transmission and reflection of ultrasonic energy is the acoustic impedance (Z). Acoustic impedance is a product of material density and sound velocity through the material:

$$Z = \rho C (\text{gcm}^{-2}\text{s}^{-1}) \quad [\text{Eq. 2}]$$

where:

$\rho$ = density (g/cm$^3$)

C = velocity (cm/s)

The acoustic impedance can be calculated for polyethylene (PE) and for ethylene propylene rubber (EPR) using the values of density and velocity of sound from the Chemical Rubber Publishing Company (CRC Handbook), Page E44. If:

$\rho_{(PE)} = 0.90$ g/cm$^3$ $C_{(PE)} = 1,950$ cm/s $\rho_{(EPR)} = 1.07$ g/cm$^3$ $C_{(EPR)} = 1,830$ cm/s Then:

$$Z_{(PE)} = (0.90)(1,950) \approx 1.8 \text{ kgcm}^{-2}\text{s}^{-1} \quad [\text{Eq. 3}]$$

$$Z_{(EPR)} = (1.07)(1,830) \approx 2 \text{ kgcm}^{-2}\text{s}^{-1} \quad [\text{Eq. 4}]$$

From the above calculations, PE is shown to have a lower acoustic impedance than EPR. Thus, PE provides a higher level of wave transmission through the material. Consequently, void images are better defined in PE than in EPR. The low acoustic impedance of a polymer enables more acoustic waves to be transmitted though the surface into the material, making internal imaging easier.

A description of each of FIGS. 6–9 is presented below:

FIG. 6

The multitude of bright spots are identified as voids. This is a reflection image of an entire cable (Sample 5 (unprepared)), immersed in a bath of water. A low-frequency transducer was used to allow penetration of sound waves through the material, resulting in a low-image resolution of the air pockets or voids.

FIG. 7

An estimated 120 spherically-shaped bright spots or voids are identified over a 0.8 cm$^3$ volume, which equates to a density of approximately 140 voids/cm$^3$. This image represents a lateral cross-sectional cut of Sample 3. The parallel lines are razor blade markings. Using the digital analyzer, void size was estimated to be at least 100 microns.

FIG. 8

An estimated 100 spherical-shaped bright spots or voids are identified over a 3.2 cm$^3$ volume, which equates to a density of about 30 voids/cm$^3$. This Figure is a magnified version of FIG. 7, captured by selecting a higher gate and adjusting the transducer positioning and system gain. Using the digital analyzer, the smallest void size was estimated to be less than 100 microns; the largest void was estimated to be 250 microns.

FIG. 9

The white speckles are voids. Verification was performed using an electron microscope.

Optical Microscopy

The optical microscope used for the tests was an Inverted Metallurgical Microscope (IMM), which is essentially a complex light microscope. The unique feature of the IMM is that the light source is projected from the bottom of the specimen, allowing the image to be observed in an erected and unreversed form.

The IMM focuses on one plane only, thereby showing a ring around the focused area. Any plane higher or lower than the focused plane is out of focus, producing blurry areas outside the ring area of the image. Consequently, FIGS. 10 through 15 are slightly blurred around the outside edges.

The light source projects a plane of light that intercepts the specimen along the plane that is in focus. This produces a focused, well-illuminated image of a specimen.

Instruments like the IMM can focus up to a magnification of about 1000×. Because of distortion and fuzziness, however, the IMM and similar instruments are commonly operated at magnifications of about 500×.

An Olympus Model PME-33 Inverted Metallurgical Microscope was used to examine the insulation samples. The IMM was also equipped with a large format and a 35 mm camera for taking pictures of the samples. The voids detected by the IMM were measured to be approximately two to five microns in diameter. Additionally, cross-section cuts, using a razor blade, appeared to contain voids of approximately the same size as those found in freeze fractures (i.e., where liquid nitrogen has been used to facilitate fracturing along crystalline pathways).

Samples 1, 3, and 8 were chosen for testing by the IMM. The following summarizes the experimental procedure used to prepare and examine cable Samples 1, 3, and 8.

For cable Samples 1 and 3, approximately 1 by 1.5-inch samples were first removed from the cable using a hack-saw. For cable Sample 8, a set of shears was used to remove the 1 by 1.5-inch section. A small groove was then cut with a razor blade on one side of the cable parallel to the axis thereof.

The specimens were quenched to 77K in a bath of liquid nitrogen until equilibrium was attained—approximately 10 minutes. The specimens were placed in a plastic bag with a razor blade inserted into the previously-cut groove. The razor blade was then struck lightly with a hammer to fracture the specimen into two pieces. Fracture surfaces were then allowed to reach room temperature prior to microscopy.

Thin sections were also prepared by cross-sectioning the specimens with a razor blade to approximately 0.5–1 mm thick.

Sample 1 was polished to a 0.5 µm surface finish. However, it was then impossible to see any surface features because the polyethylene smeared and debris gathered in possible void sites. Consequently, the Samples were not polished for the examinations.

For testing, to obtain a uniform focal length, fracture surfaces were chosen that had fairly flat surface features. The fracture surfaces were cleaned of debris and condensation using compressed air.

The Samples were placed on the microscope so that only the edges of the fracture surface contacted the edges of the specimen stage. The entire fracture surface was scanned at 50× and 100× to determine the features on which to focus. Photographs were taken at magnification level of 200× and 500×.

Higher magnification photographs were not taken because the focal length of an optical microscope is too short to allow surfaces with non-uniform heights to come into focus. Suspected voids were identified by a combination of shape and focal length using various degrees of polarized light in the optical microscope.

Six photographs of the Samples are provided as FIGS. 10–15. Numerous voids are shown to be present in the insulation materials of the Samples. Each of FIGS. 10–15 is described below:

FIG. 10

There are an estimated 50 voids, identified over a 0.1 cm$^3$ volume, which equates to a density of approximately 500 voids/cm$^3$. The parallel lines are razor blade markings. The scale shown (closer to the left edge) is one centimeter. It is estimated that the smallest void is about 5 microns and the largest is about 10 microns.

FIG. 11

Figure 11:
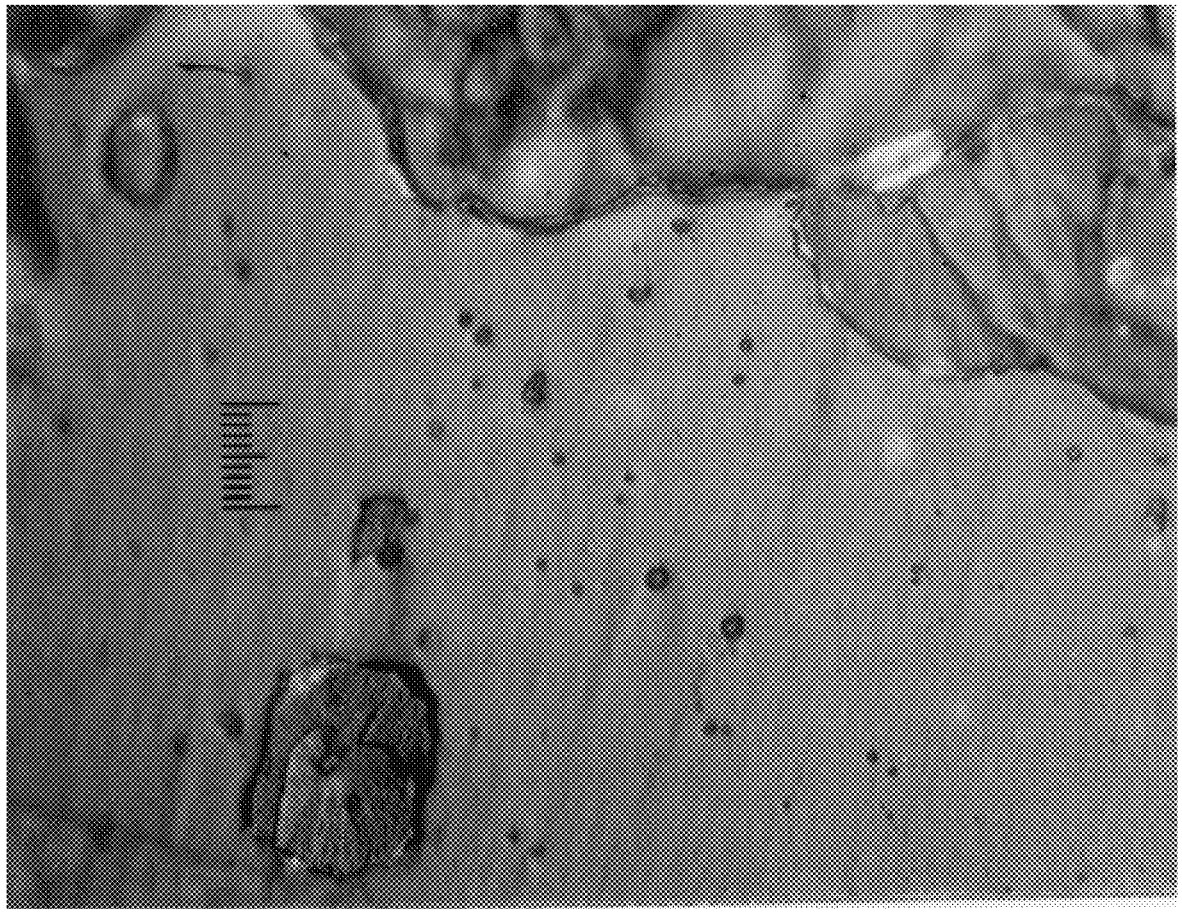
FIG. 11 is an optical image of Sample 3 at 500×.

There are an estimated 30 voids, identified over a 0.03 cm$^3$ volume. Correspondingly, this equates to a density of about 1000 voids/cm$^3$. FIG. 11 illustrates a freeze fracture surface of a lateral cross-sectional cut. The scale shown (at the left edge) is one centimeter. It is estimated that the smallest void is about 2 microns and the largest is about 4 microns.

FIG. 12

Figure 12:
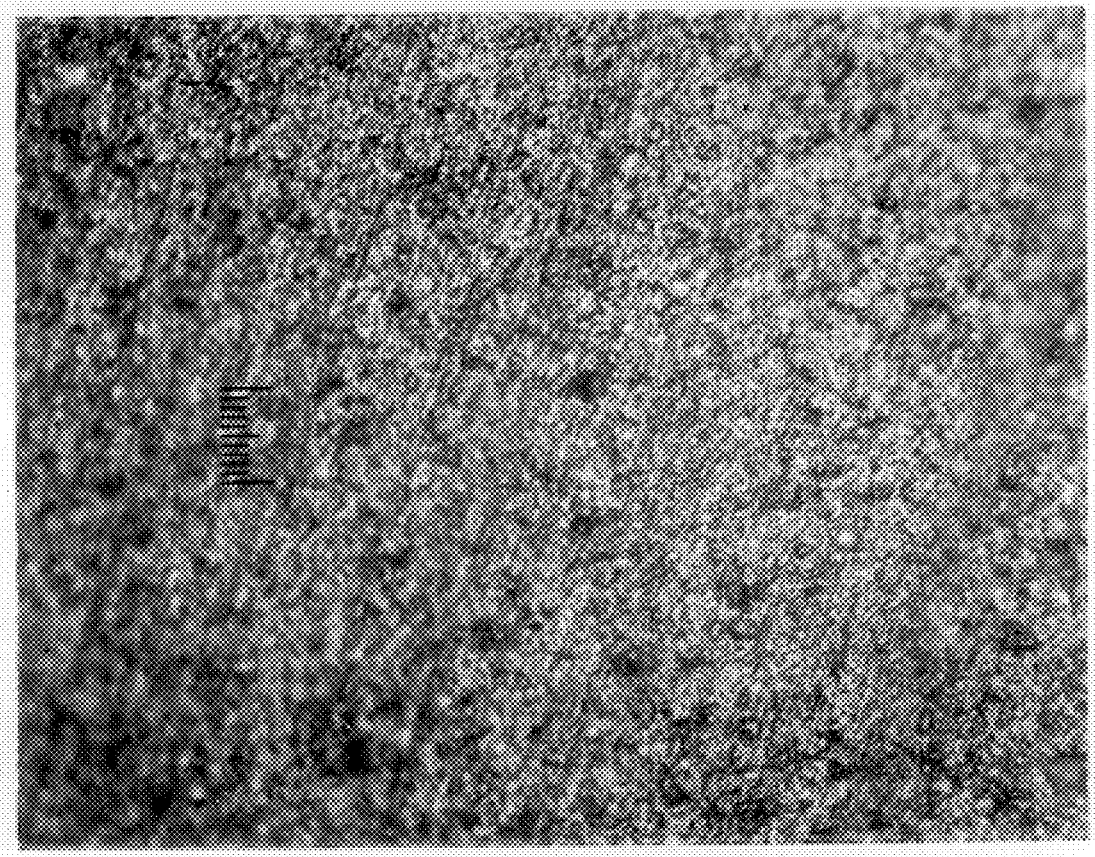
FIG. 12 is an optical image of Sample 8 at 200×.

Estimates indicate that there are about 10 spherical-shaped voids identified over a 0.1 cm$^3$ volume, which equates to a density of approximately 100 voids/cm$^3$. FIG. 12 represents a lateral cross-sectional cut with a razor blade. The parallel lines shown in FIG. 12 are razor blade markings. With a scale of one centimeter, it is estimated that the smallest void is about 5 microns and the largest is about 15 microns.

FIG. 13

Figure 13:
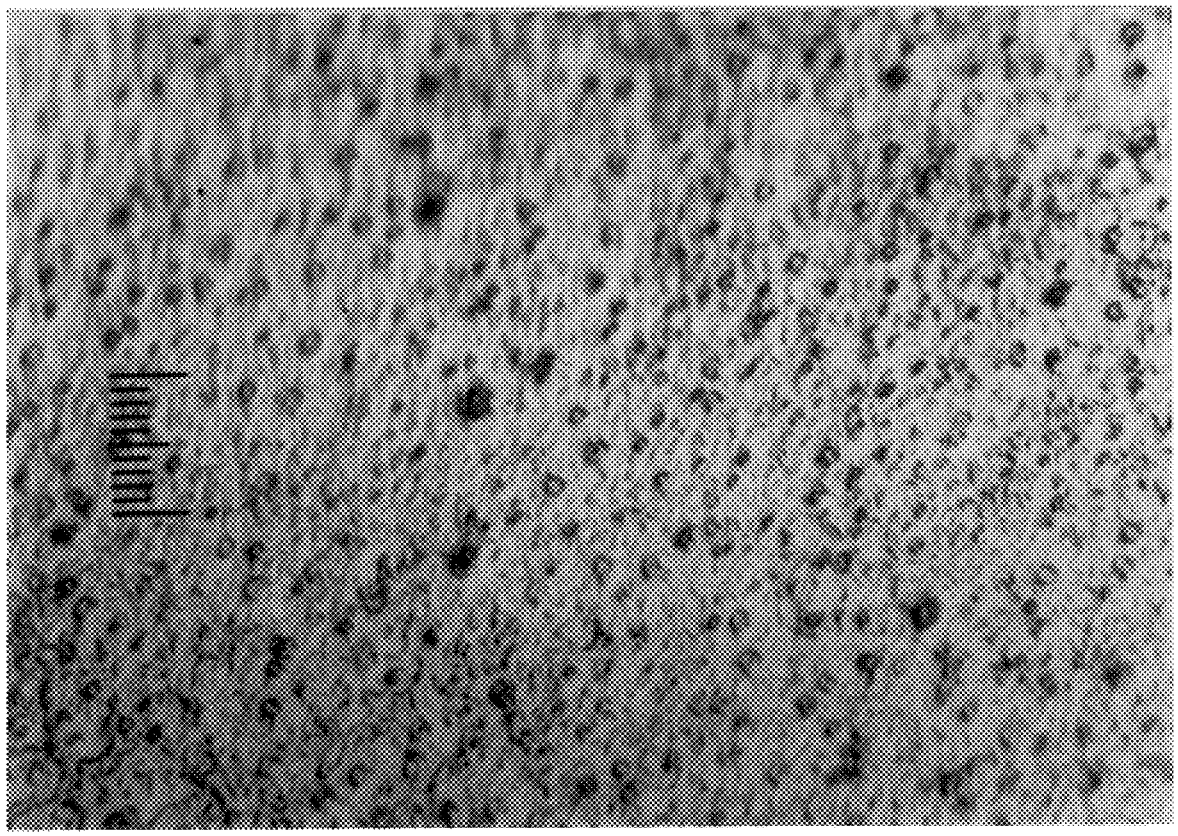
FIG. 13 is an optical image of Sample 1 at 500×.

There are an estimated 50 spherical voids, identified over a 0.1 cm$^3$ volume, which equates to a density of approximately 500 voids/cm$^3$. FIG. 13 depicts a freeze fracture-surface of a lateral cross-sectional cut. With a scale of 1½ cm, it is estimated that the smallest void is about 4 microns and the largest is about 8 microns.

FIG. 14

Figure 14:
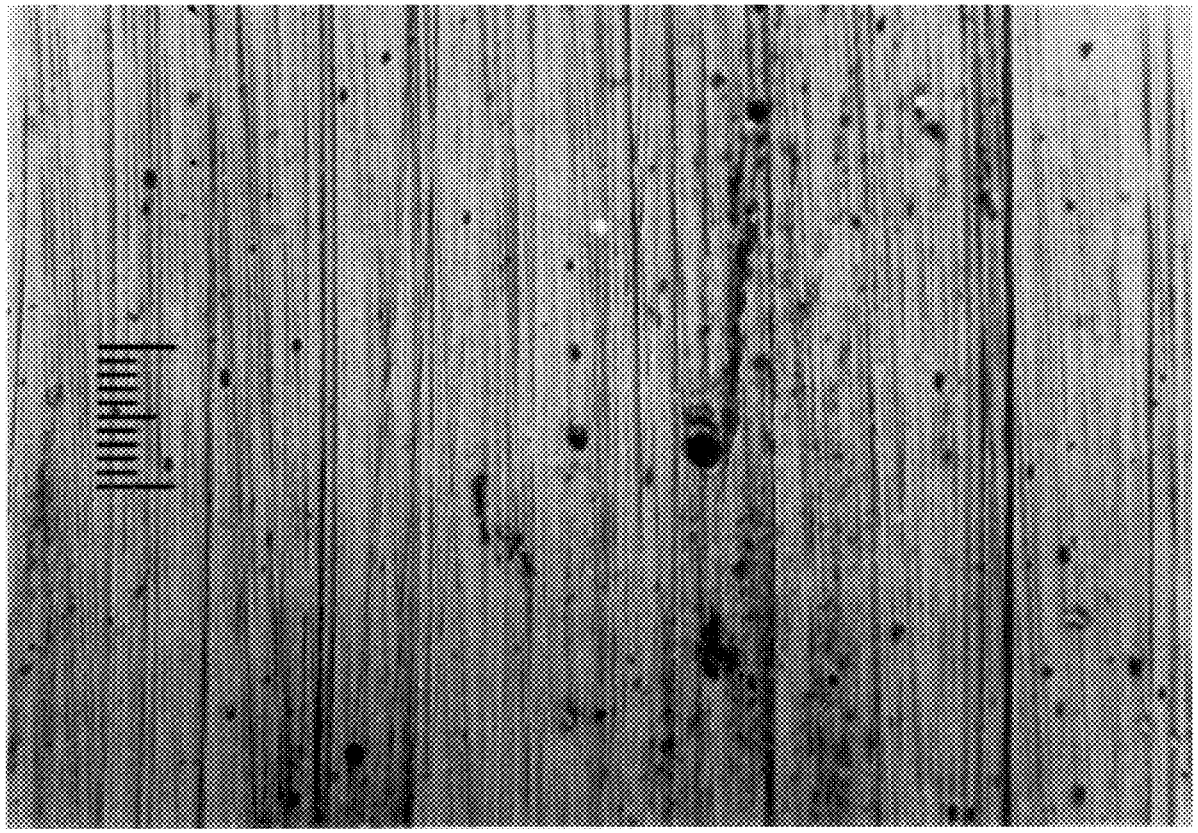
FIG. 14 is an optical image of Sample 3 at 200×.

There are an estimated 45 voids, identified over a 0.2 cm$^3$ volume, which equates to a density of approximately 225 voids/cm$^3$. FIG. 14 illustrates a lateral cross-sectional cut with a razor blade. The parallel lines shown in FIG. 14 are razor blade markings. With the 1½ cm scale shown, it is estimated that the smallest void is about 5 microns and the largest is about 20 microns.

FIG. 15

Figure 15:
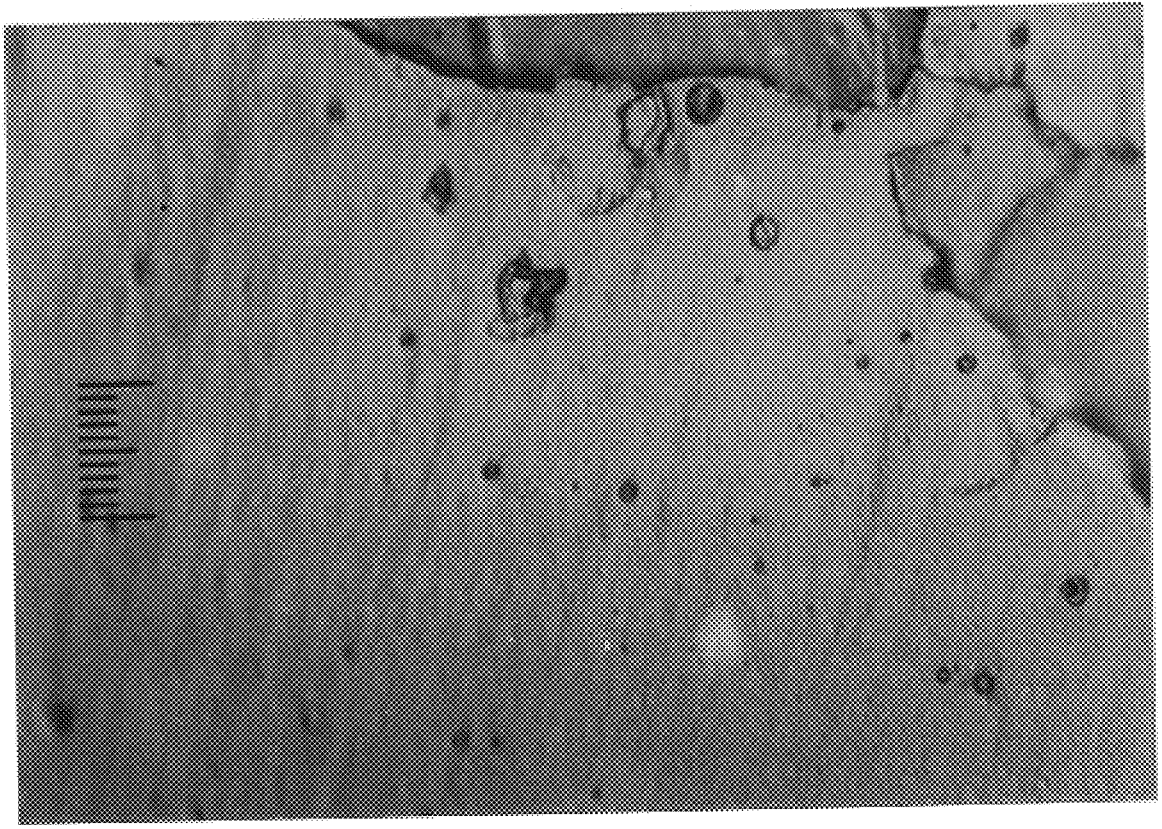
FIG. 15 is an optical image of Sample 3 at 500×.

There are an estimated 25 voids, identified over a 0.1 cm$^3$ volume, which equates to a density of approximately 250 voids/cm$^3$. FIG. 15 represents a freeze fracture surface of a lateral cross-sectional cut. With the scale of 1½ cm, it is estimated that the smallest void is about 2 microns and the largest is about 8 microns.

Scanning Electron Microscopy

The Scanning Electron Microscope (SEM) uses an electron beam that moves over the specimen surface in a series of parallel lines. Simultaneously, a point of light on a television-like screen moves in the same pattern. The SEM views only a small portion of the specimen's surface at a time. The final image is a composite of the pictures of the many small sections individually viewed in turn. The specimen surface is subdivided into small squares; the length of each square is equal to the limit of instrument resolution.

Each of the specimen squares is bombarded in turn by an electron probe, the cross-sectional area of which is approximately equal to the area of each square. Wherever the probe strikes the specimen, secondary electrons are emitted. The number of emitted secondary electrons is determined primarily by the chemical nature of the specimen's surface structure.

Photograph resolution and quality are determined by the number of secondary electrons that reflect from each point of the sample. For example, the picture will be bright where many electrons are reflected from the specimen; the picture will be less bright where only a small number of electrons are reflected.

Image formation in a SEM differs from that in an optical microscope. In a SEM, the image is formed on a cathode ray tube after information is converted from the specimen surface into a train of electrical signals. The SEM thus displays an image which is similar to one that views an object in light. This allows surface contours of little craters and impressions to be revealed.

An Hitachi S-800 Scanning Electron Microscope was used to study fracture surfaces of Samples 1, 6, and 8. The SEM analysis was successful in detecting, imaging, and measuring voids as small as 0.4 micron. Photographs of the Samples were taken with Polaroid Type 55 black and white professional film at magnification levels as high as 12000×. Generally, however, the photographs were taken at lower magnification levels of less than 2000×.

The Samples were tracked using a six-digit code (e.g., 080205), which is placed on the photograph's lower left corner. The following provides a description of the code:

For example, if the code is 080205, then:

08 is the sample number 02 refers to either lateral or longitudinal cross-section where:

01—refers to lateral cross-section normal to the axial direction of the cable, and 02—refers to the longitudinal cross-section parallel to the axial direction of the cable.

05 is the sequential picture number taken for that sample.

The code on the right lower corner of the photographs indicates the magnification level (e.g., x500 means 500x). The number next to the magnification level provides the scale (e.g., 60 μm means 60 microns) for the line of periods above it. The length of the scale is 32 mm.

The notation between the six-number code and the magnification level refers to the operating voltage (e.g., 2 kV means that the operating voltage was at 2 kilovolts).

Because the SEM has much higher resolution capability than the optical microscope, Samples 1, 6, and 8 were selected for the SEM examination. This sample collection consisted of one sample each of aged and new polyethylene and one sample of new ethylene propylene rubber.

The following discussion summarizes the procedures used for sample preparation, microscopic examination, and scanning.

Direct observation with the SEM requires that the specimens be coated with a thick layer of conductive material (such as gold) and that low voltages be used to reduce specimen charging. The SEM tests used freeze-fracture techniques (similar to that of the optical examination) to form the specimen surfaces of Samples 1, 6, and 8.

The freeze-fracture specimens were prepared using a procedure similar to that described above. The Samples were then trimmed of excess material until the fracture surface thickness was approximately 2–4 mm. An Hitachi 10 mm SEM stub was placed in a beaker of acetone, cleaned in an ultrasonicator for 10 minutes, and then airdried.

Using a pair of latex gloves, a piece of carbon tape was placed on the SEM stub and the backing removed. Using a pair of forceps, the fracture surface was carefully placed upon the carbon tape, affixing it in position. Carbon paste was painted on the edges of the fracture surface to provide conduction. The Samples were placed in a vacuum chamber for two days to remove any excess gases.

The Samples were placed in a sputter deposition system for one minute at a potential of 8V with a current of 10 milliamperes to coat the surface with approximately 100 Å of Au—Pd (Gold-Platinum).

The SEM was operated at a voltage of 2 kV and at a working distance of 5 mm from the Samples. The apertures were adjusted from 15 mm to 5 mm to ensure proper alignment and the stigmators were adjusted at 20000x to ensure proper resolution. Subsequently, the focus was adjusted as high as 20000x.

The Samples' surfaces were scanned at the lowest magnification (70x) to find interesting surfaces to magnify. Generally, the highest scan rate was used (TV scan), but scan rates were varied to enhance surface features and to remove noise from the images. Fracture surfaces were magnified as high as 15000x to enhance the surface features. In addition, some degree of sample tilt relative to the viewing lens was used to enhance the surface features.

Voids were identified in Samples 1, 6, and 8. The samples were scanned under different magnifications to enhance the surface features when spherical cavities or voids were located. The hollow openings of the voids were clearly seen and could be measured using a micron scale embodied within the picture.

The results of the SEM examination prove that spherical-shaped voids exist inside conductor insulation material. Voids as small as 0.3 micron and as large as 12 micron exist, and there is a certain density (the pattern of voids are consistent) within the material.

Figure 16:
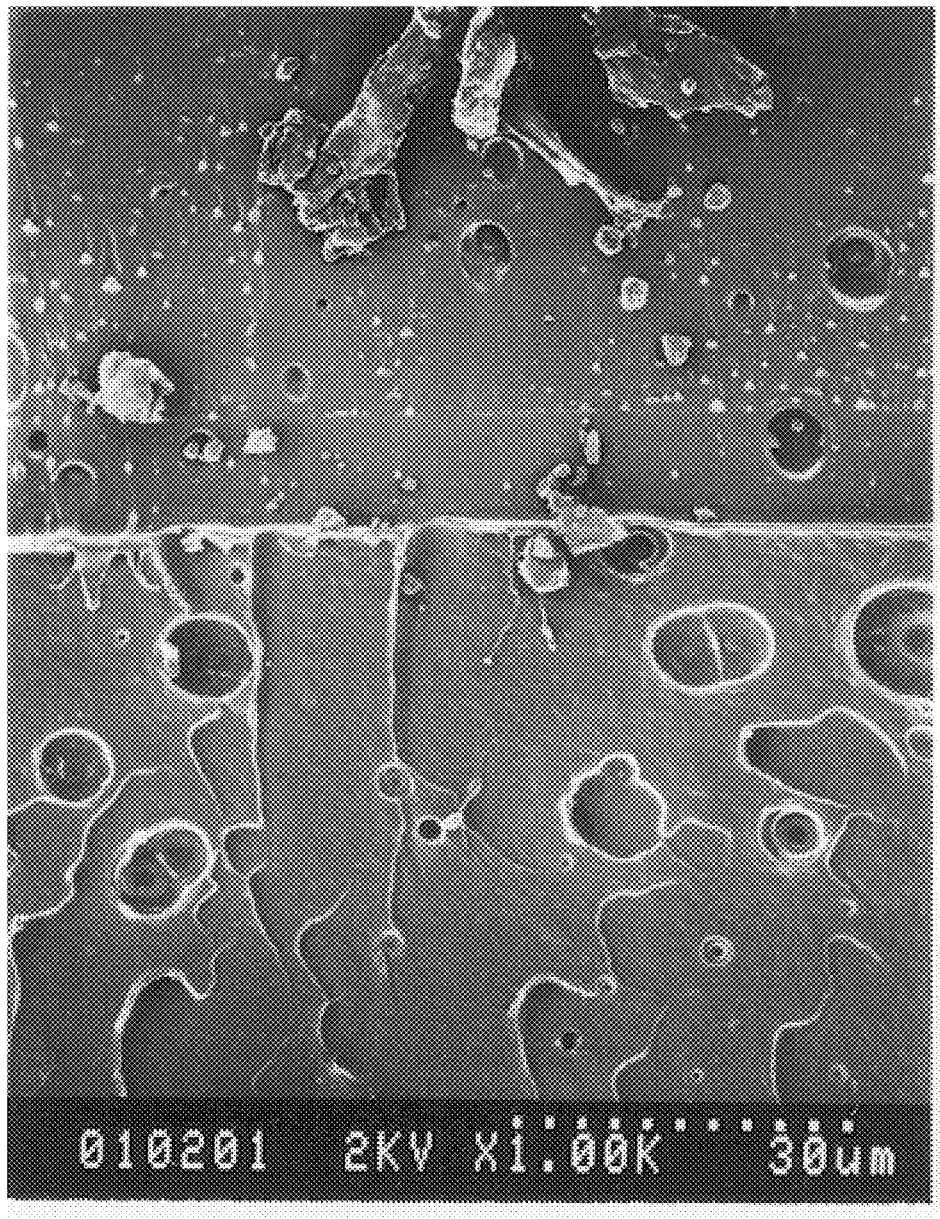
FIG. 16 is a scanning electron microscopic image of Sample 1 at 1000×.
Figure 17:
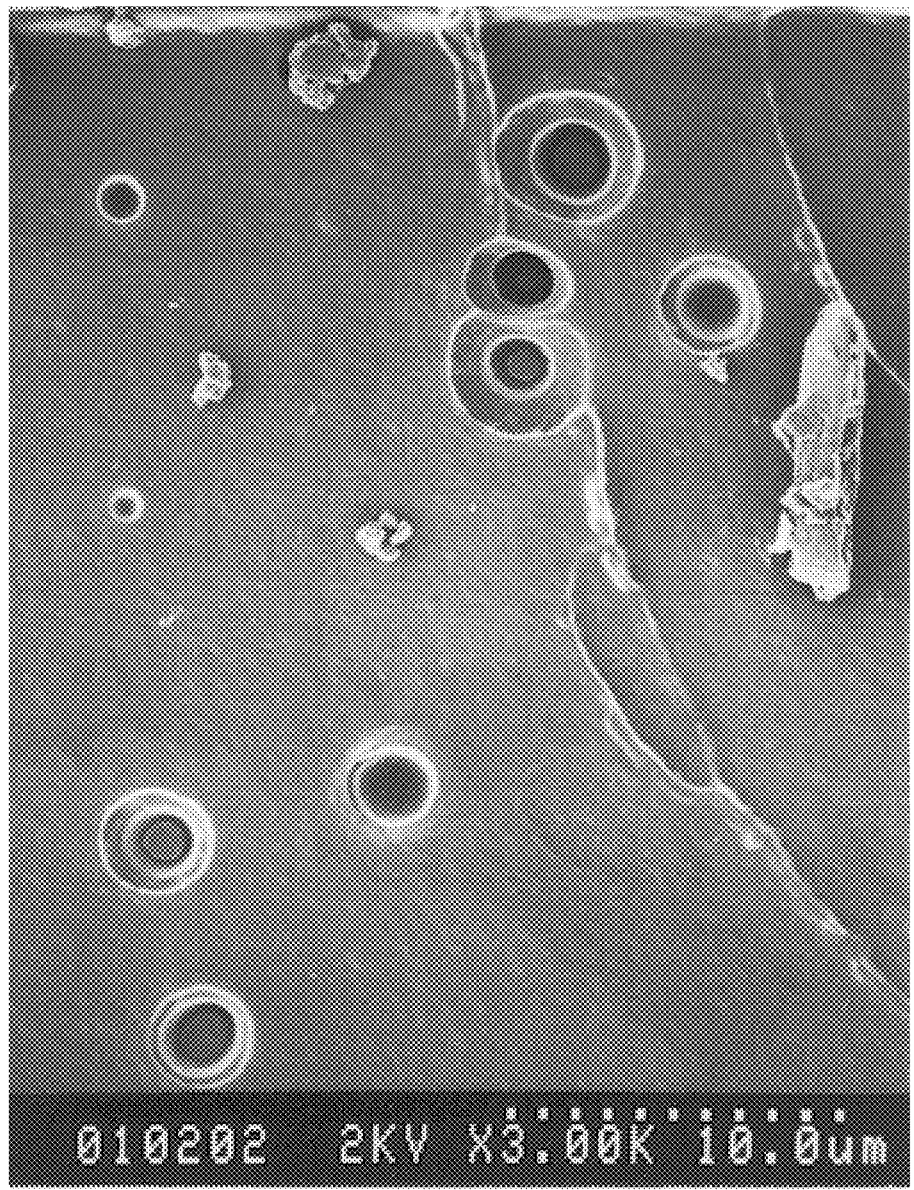
FIG. 17 is a scanning electron microscopic image of Sample 1 at 3000×.
Figure 18:
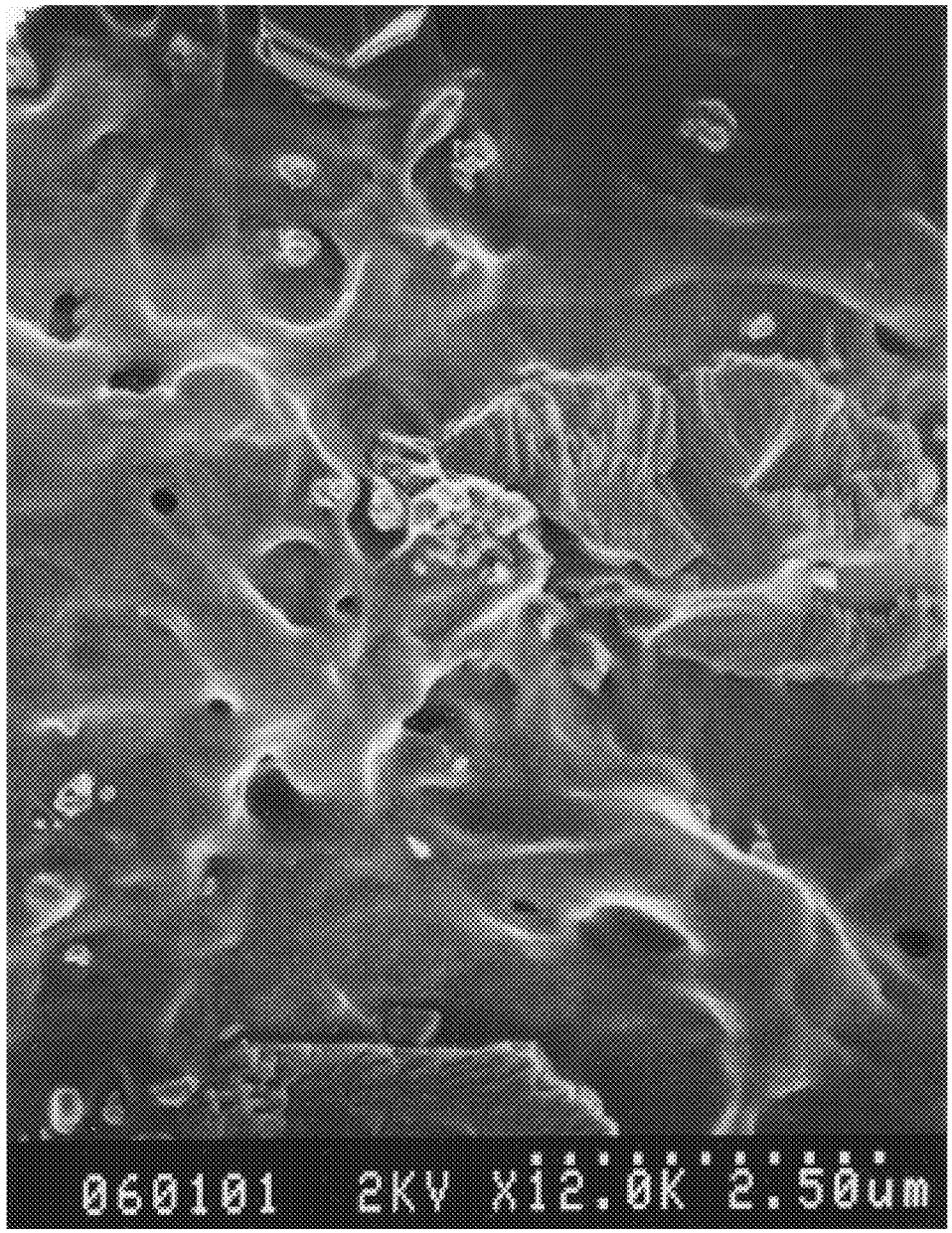
FIG. 18 is a scanning electron microscopic image of Sample 6 at 12000×.
Figure 19:
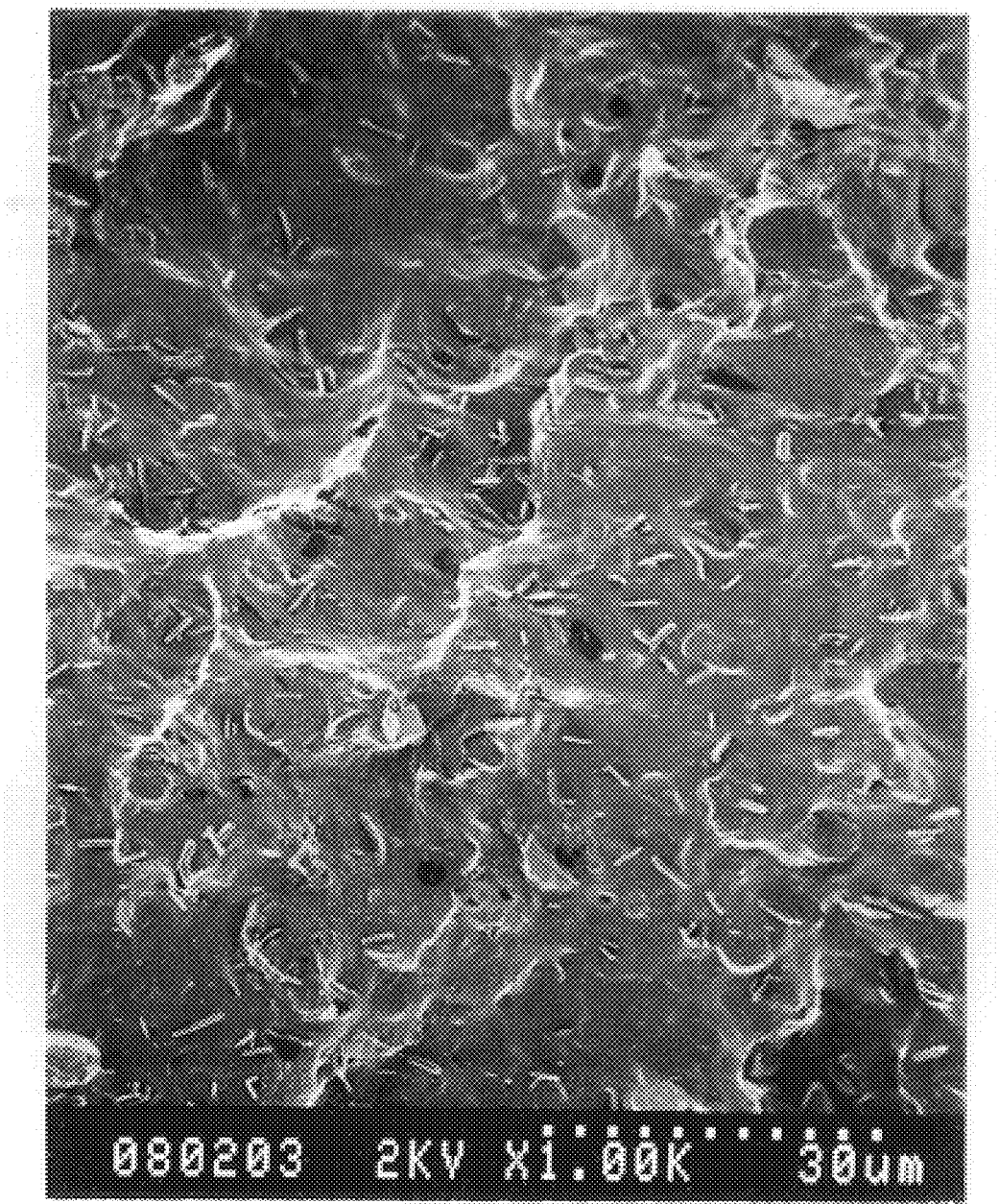
FIG. 19 is a scanning electron microscopic image of Sample 8 at 1000×.
Figure 20:
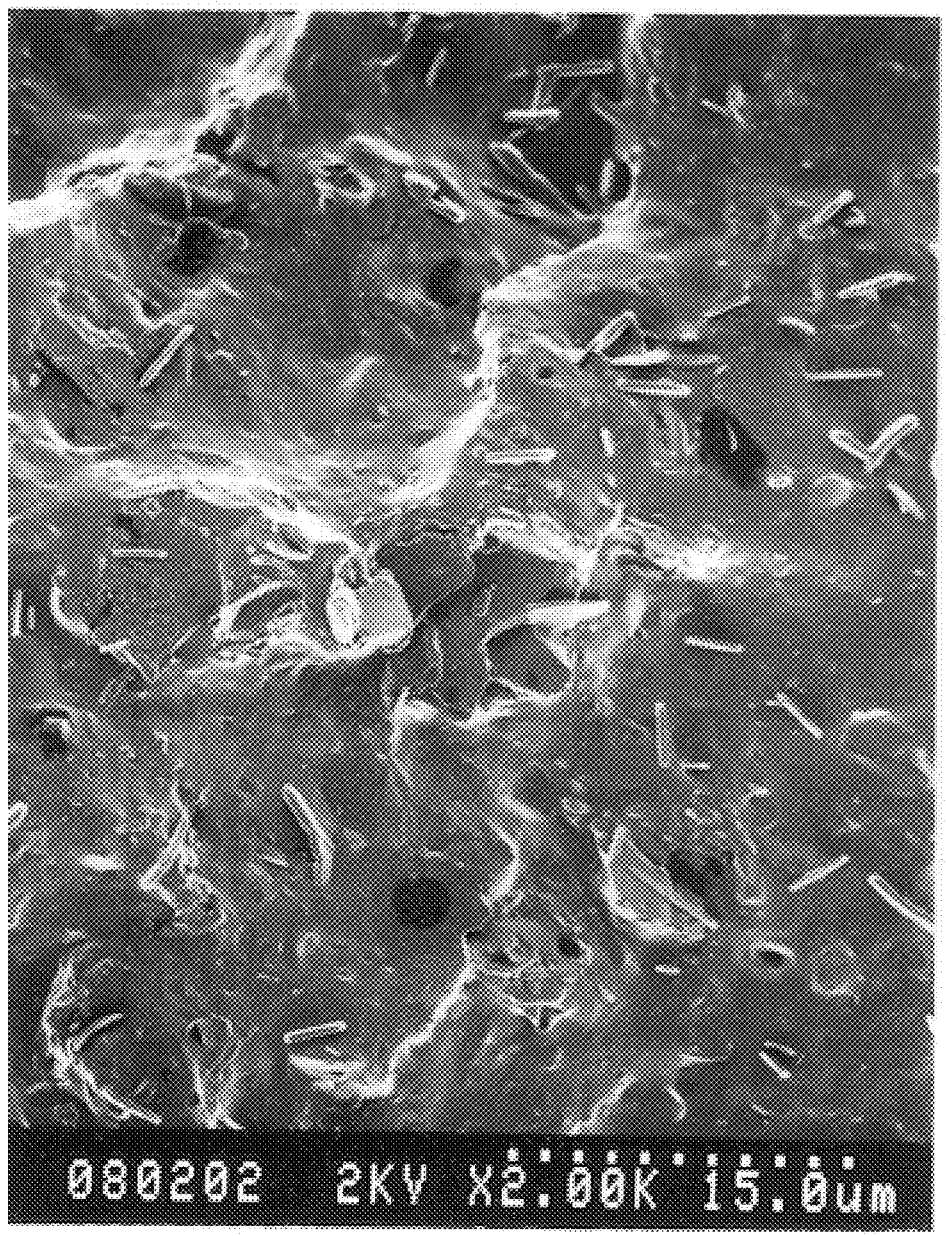
FIG. 20 is a scanning electron microscopic image of Sample 8 at 2000×.

For example, FIGS. 16 and 17 show entire spherical, contour-shaped cavities grouped in a pattern in two different areas of Sample 1. FIG. 18 shows entire spherical-shaped cavities grouped in a pattern in Sample 6. FIGS. 19 and 20 show much smaller cavities in a grouped pattern in Sample 8. The fact that void size is smaller in the new cable insulator supports the theory that void size increases with age. However, other possible causes of smaller void sizes include improved manufacturing processes and addition of fillers in the insulation material.

Each of FIGS. 16–20 is described below.

FIG. 16

An estimated 33 spherical voids are identified over a 0.05 $cm^3$ volume, which corresponds to a density of about 660 voids/$cm^3$. FIG. 16 represents a longitudinal cross-sectional cut. The top portion is smoother since it is cut with a razor blade. The bottom portion is a freeze-fracture. The scale at the lower right of the micrograph is 30 μm. The smallest void identified is about 0.5 micron, while the largest void is estimated to be 12 microns.

FIG. 17

An estimated 9 spherical voids are identified over a 0.03 $cm^3$ volume, which corresponds to a density of about 300 voids/$cm^3$. FIG. 17 depicts a freeze-fracture surface of a longitudinal cross-sectional cut. The circular anomalies inside the voids were examined with a high (i.e., 15000x) magnification. Nothing internally was revealed in the void. With a scale of 10 μm, the smallest void identified is about 2 microns; the largest void is estimated to be 4.5 microns.

FIG. 18

An estimated 12 spherical voids are identified over a 0.004 $cm^3$ volume, which relates to a density of approximately 3000 voids/$cm^3$. FIG. 18 illustrates a freeze-fracture surface of a lateral cross-sectional cut. The smallest void identified with a scale of 2.5 μm is about 0.3 micron. The largest void is estimated to be 0.5 micron.

FIG. 19

An estimated 35 spherical voids are identified over a 0.05 $cm^3$ volume, which relates to a density of about 700 voids/$cm^3$. FIG. 19 depicts a freeze-fracture surface of a longitudinal cross-sectional cut. The pellet-shaped items in FIGS. 19 and 20 are filler materials. Discussions with Rockbestos, the manufacturer of the cable Samples tested, revealed that Rockbestos uses a Translink-37 surface-treated clay in its cable to improve the bonding of the polymer chains, thereby increasing cable strength. At a micrograph scale of 30 μm, the smallest void identified is about 2.5 microns. The largest void is estimated to be 6.5 microns.

FIG. 20

An estimated 20 spherical voids are identified over a 0.02 $cm^3$ volume, which relates to a density of about 1000 voids/$cm^3$. FIG. 20 is a higher magnification of FIG. 19. Thus, the voids and filler material as described above can be seen more clearly in FIG. 20. The scale at the lower right is 15 μm. The smallest void identified is about 1.5 microns. The largest void is estimated to be 3.0 microns.

As related above, various testing techniques were conducted to determine which could detect and measure micron-size voids inside conductor insulation material. Two nondestructive techniques (conventional ultrasound and acoustical microscopy) were evaluated, along with two destructive techniques (optical microscopy and scanning electron microscopy).

Preferably, acoustical microscopy may be used for detecting and measuring micron-size voids within insulation material. This method uses an acoustic micro-imaging (reflection) technique that is sensitive to material discontinuities in the micron range.

Optical microscopy and scanning electron microscopy analysis confirmed the following: (1) voids exist within conductor insulation material; (2) micron-size voids can be detected; and (3) a definite formation of voids (absolute density) exists.

While optical microscopy and scanning electron microscopy were able to detect and measure micron-sized voids, it is probably not practical to use these methods in industrial settings.

The various test results for examining the Samples of polyethylene (PE) and ethylene propylene rubber (EPR) are presented in FIG. 21.

The cable industry has made many advances over the years in cable manufacturing. However, even with advancements, micron-size voids still remain within conductor insulation systems. Because cable failures may be caused by discharges in a single void in an otherwise sound insulation system, it is important to detect voids that can impair insulation life. Detection is preferably accomplished by a nondestructive technique, such as acoustical microscopy, that is capable of furnishing internal images that allow void size and formation to be viewed and evaluated.

As a result of the tests, the following conclusions may be drawn: (1) micron-size voids exist and can be detected within the insulation system of new and aged cable; (2) void density was found to be consistent or relatively uniform; and (3) acoustical microscopy is the preferred method for detecting and generating internal images of micron-size voids within a conductor insulation system, and it can feasibly be used for field testing.

It should be appreciated that the present invention may be modified or configured as appropriate for the application. The embodiments described above are to be considered in all respects only as illustrative and not restrictive. The scope of the invention is indicated by the following claims rather than by the foregoing description. All changes which come within the literal meaning as well as the range of equivalency of the claims are to be embraced within their scope.

What is claimed and desired to be secured by Letters Patent of the United States is:

1. A method of detecting and measuring internal voids in insulation material, comprising the following steps:

providing at least one sample of an insulation material surrounding a metallic conductor;

providing an acoustical imaging system comprising a transducer for generating at least one image of the at least one sample of the insulation material, the transducer operable to send and to detect reflected acoustic waves;

analyzing the at least one image to detect the presence of internal voids therein; and measuring the internal voids present in the at least one sample to determine their size, volume and density therein.

2. The method of claim 1 wherein the imaging system comprises a nondestructive imaging system.

3. The method of claim 1 wherein the imaging system comprises an acoustical microscopy system.

4. The method of claim 1, further comprising the step of measuring the density of the voids present in the at least one sample of the insulation material.

5. The method of claim 4, further comprising the step of analyzing the size and density of voids present in the at least one sample of the insulation material to confirm the operability thereof.

6. The method of claim 1 wherein the at least one sample of the insulation material comprises a plurality of samples.

7. A method of establishing void parameters for insulation material, comprising the following steps:

providing a plurality of samples of an insulation material surrounding a metallic conductor;

providing an acoustical imaging system comprising a transducer for generating at least one image of each of the plurality of samples, the transducer operable to send and to detect reflected acoustic waves;

analyzing the at least one image of each of the plurality of samples to detect the presence of internal voids therein;

analyzing the internal voids to determine at least two void parameters of size, volume and density for each of the plurality of samples; and comparing the one or more void parameters for each of the plurality of samples to determine the limiting void parameters among the plurality of samples.

8. The method of claim 7, further comprising the step of utilizing the correlation between the limiting void parameters and the design or required electric field to derive a model for the level of operability of the insulation material as a function of the one or more void parameters.

9. The method of claim 7 wherein the one or more void parameters are selected from the group consisting of void size and void density.

10. A method of detecting and measuring voids in insulation material, comprising the following steps:

providing at least one sample of an insulation material surrounding a metallic conductor;

providing a nondestructive acoustical imaging system comprising a transducer for generating one or more images of the at least one sample of the insulation material, the transducer operable to send and to detect reflected acoustic waves;

analyzing the one or more images to detect the presence of internal voids therein;

measuring one or more of at least the size, volume and density of the internal voids present in the at least one sample;

determining the limiting combination of void size, volume and density among the measured samples; and deriving a model for the level of operability of the insulation material as a function of one or more of at least the size, volume and density of the internal voids detected in the at least one sample and the design or required electric field.

11. The method of claim 10 wherein the at least one sample of the insulation material comprises a plurality of samples.

* * * * *